(12) United States Patent
Pastore et al.

(10) Patent No.: US 8,615,296 B2
(45) Date of Patent: *Dec. 24, 2013

(54) METHOD AND APPARATUS FOR CLOSED-LOOP INTERMITTENT CARDIAC STRESS AUGMENTATION PACING

(75) Inventors: Joseph M. Pastore, Woodbury, MN (US); Tamara Colette Baynham, Blaine, MN (US); Donald L. Hopper, Maple Grove, MN (US); Allan C. Shuros, St. Paul, MN (US); Shantha Arcot-Krishnamurthy, Roseville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 933 days.

This patent is subject to a terminal disclaimer.

(21) Appl. No.: 11/682,448

(22) Filed: Mar. 6, 2007

(65) Prior Publication Data
US 2008/0221636 A1 Sep. 11, 2008

(51) Int. Cl.
*A61N 1/362* (2006.01)
(52) U.S. Cl.
USPC .............................. 607/9; 607/17
(58) Field of Classification Search
USPC .................... 607/9, 14, 17–19, 23
See application file for complete search history.

(56) References Cited

U.S. PATENT DOCUMENTS

| 4,587,975 A | 5/1986 | Salo et al. |
|---|---|---|
| 4,722,342 A | 2/1988 | Amundson |
| 4,730,619 A | 3/1988 | Koning et al. |
| 4,834,710 A | 5/1989 | Fleck |
| 4,919,133 A | 4/1990 | Chiang |
| 5,007,427 A | 4/1991 | Suzuki et al. |
| 5,014,702 A | 5/1991 | Alt |
| 5,072,458 A | 12/1991 | Suzuki |
| 5,111,818 A | 5/1992 | Suzuki et al. |
| 5,135,004 A | 8/1992 | Adams et al. |
| 5,184,615 A | 2/1993 | Nappholz et al. |
| 5,199,428 A | 4/1993 | Obel et al. |
| 5,282,840 A | 2/1994 | Hudrlik |

(Continued)

FOREIGN PATENT DOCUMENTS

| EP | 0879618 A1 | 11/1998 |
|---|---|---|
| EP | 2000078391 A1 | 12/2000 |

(Continued)

OTHER PUBLICATIONS

"U.S. Appl. No. 11/129,050, Supplemental Amendment and Response filed Sep. 12, 2008 to Final Office Action mailed May 12, 2008 and the Advisory Action mailed Jul. 28, 2008", 12 pgs.

(Continued)

*Primary Examiner* — Joseph Stoklosa
(74) *Attorney, Agent, or Firm* — Schwegman Lundberg & Woessner, P.A.

(57) ABSTRACT

A cardiac pacing system controls the progression of a cardiac disorder such as heart failure by delivering cardiac pacing to create or augment regional stress in the heart. The cardiac pacing is delivered intermittently, such as on a periodic basis, according to a cardiac stress augmentation pacing sequence that includes alternating pacing and non-pacing periods. One or more physiological signals are monitored for closed-loop control of the cardiac pacing using baseline characteristics of the cardiac disorder, acute cardiac stress created by the cardiac pacing, and/or risk associated with the cardiac pacing.

31 Claims, 9 Drawing Sheets

(56) References Cited

U.S. PATENT DOCUMENTS

| | | | |
|---|---|---|---|
| 5,313,953 A | 5/1994 | Yomtov et al. | |
| 5,360,436 A | 11/1994 | Alt et al. | |
| 5,376,106 A | 12/1994 | Stahmann et al. | |
| 5,391,188 A * | 2/1995 | Nelson et al. | 607/9 |
| 5,484,419 A | 1/1996 | Fleck | |
| 5,531,768 A | 7/1996 | Alferness | |
| 5,588,432 A | 12/1996 | Crowley | |
| 5,634,899 A | 6/1997 | Shapland et al. | |
| 5,649,968 A | 7/1997 | Alt et al. | |
| 5,755,671 A | 5/1998 | Albrecht et al. | |
| 5,919,209 A | 7/1999 | Schouten | |
| 6,021,350 A | 2/2000 | Mathson | |
| 6,104,956 A | 8/2000 | Naritoku et al. | |
| 6,108,577 A | 8/2000 | Benser | |
| 6,115,628 A | 9/2000 | Stadler et al. | |
| 6,208,894 B1 | 3/2001 | Schulman et al. | |
| 6,233,486 B1 | 5/2001 | Ekwall et al. | |
| 6,238,422 B1 | 5/2001 | Van Oort | |
| 6,256,538 B1 | 7/2001 | Ekwall | |
| 6,272,379 B1 | 8/2001 | Fischell et al. | |
| 6,278,894 B1 | 8/2001 | Salo et al. | |
| 6,285,907 B1 | 9/2001 | Kramer et al. | |
| 6,314,323 B1 | 11/2001 | Ekwall et al. | |
| 6,368,284 B1 | 4/2002 | Bardy | |
| 6,408,208 B1 | 6/2002 | Sun | |
| 6,445,953 B1 | 9/2002 | Bulkes et al. | |
| 6,477,402 B1 | 11/2002 | Lynch et al. | |
| 6,501,983 B1 | 12/2002 | Natarajan et al. | |
| 6,569,145 B1 | 5/2003 | Shmulewitz et al. | |
| 6,584,362 B1 | 6/2003 | Scheiner et al. | |
| 6,604,000 B2 | 8/2003 | Lu | |
| 6,610,713 B2 | 8/2003 | Tracey | |
| 6,628,988 B2 | 9/2003 | Kramer et al. | |
| 6,711,436 B1 | 3/2004 | Duhaylongsod | |
| 6,735,479 B2 | 5/2004 | Fabian et al. | |
| 6,763,267 B2 | 7/2004 | Ding | |
| 6,813,516 B2 | 11/2004 | Ujhelyi et al. | |
| 6,827,690 B2 | 12/2004 | Bardy | |
| 6,838,471 B2 | 1/2005 | Tracey | |
| 6,842,642 B2 | 1/2005 | Vanhout | |
| 6,845,267 B2 | 1/2005 | Harrison et al. | |
| 6,865,420 B1 | 3/2005 | Kroll | |
| 6,892,095 B2 | 5/2005 | Salo | |
| 6,907,285 B2 | 6/2005 | Denker et al. | |
| 6,913,577 B2 | 7/2005 | Bardy | |
| 6,937,899 B2 | 8/2005 | Sheldon et al. | |
| 6,950,701 B2 | 9/2005 | Begemann et al. | |
| 6,965,797 B2 | 11/2005 | Pastore et al. | |
| 6,973,349 B2 | 12/2005 | Salo | |
| 7,010,345 B2 | 3/2006 | Hill et al. | |
| 7,039,462 B2 | 5/2006 | Pastore et al. | |
| 7,043,305 B2 | 5/2006 | Kenknight et al. | |
| 7,062,314 B2 | 6/2006 | Zhu et al. | |
| 7,062,325 B1 | 6/2006 | Krig et al. | |
| 7,069,070 B2 | 6/2006 | Carlson et al. | |
| 7,072,711 B2 | 7/2006 | Girouard et al. | |
| 7,171,258 B2 | 1/2007 | Goode | |
| 7,215,992 B2 | 5/2007 | Stahmann et al. | |
| 7,215,997 B2 | 5/2007 | Yu et al. | |
| 7,277,761 B2 | 10/2007 | Shelchuk | |
| 7,295,874 B2 * | 11/2007 | Prinzen et al. | 607/17 |
| 7,299,087 B2 | 11/2007 | Bardy | |
| 7,340,303 B2 | 3/2008 | Zhu | |
| 7,364,547 B2 | 4/2008 | Stahmann et al. | |
| 7,366,568 B2 | 4/2008 | Pastore et al. | |
| 7,437,191 B2 * | 10/2008 | Pastore et al. | 607/9 |
| 7,460,906 B2 | 12/2008 | Libbus | |
| 7,479,112 B2 | 1/2009 | Sweeney et al. | |
| 7,486,991 B2 | 2/2009 | Libbus et al. | |
| 7,668,594 B2 | 2/2010 | Brockway et al. | |
| 7,894,896 B2 | 2/2011 | Baynham et al. | |
| 7,917,210 B2 | 3/2011 | Baynham et al. | |
| 7,979,123 B2 | 7/2011 | Prinzen et al. | |
| 2002/0042632 A1 | 4/2002 | Iaizzo et al. | |
| 2002/0072777 A1 | 6/2002 | Lu | |
| 2002/0082660 A1 | 6/2002 | Stahmann et al. | |
| 2002/0123772 A1 | 9/2002 | Sun et al. | |
| 2002/0128563 A1 | 9/2002 | Carlson et al. | |
| 2003/0004549 A1 | 1/2003 | Hill et al. | |
| 2003/0009189 A1 | 1/2003 | Gilson et al. | |
| 2003/0045908 A1 | 3/2003 | Condie et al. | |
| 2003/0055461 A1 | 3/2003 | Girouard et al. | |
| 2003/0060854 A1 | 3/2003 | Zhu | |
| 2003/0120313 A1 | 6/2003 | Begemann et al. | |
| 2003/0120315 A1 | 6/2003 | Spinelli et al. | |
| 2003/0139778 A1 | 7/2003 | Fischell et al. | |
| 2003/0158492 A1 | 8/2003 | Sheldon et al. | |
| 2003/0158584 A1 | 8/2003 | Cates et al. | |
| 2003/0204206 A1 | 10/2003 | Padua et al. | |
| 2003/0204231 A1 | 10/2003 | Hine et al. | |
| 2003/0233130 A1 | 12/2003 | Padmanabhan et al. | |
| 2004/0015081 A1 | 1/2004 | Kramer et al. | |
| 2004/0038947 A1 | 2/2004 | Wink et al. | |
| 2004/0049235 A1 * | 3/2004 | Deno et al. | 607/9 |
| 2004/0088017 A1 | 5/2004 | Sharma et al. | |
| 2004/0102815 A1 | 5/2004 | Balczewski et al. | |
| 2004/0106960 A1 | 6/2004 | Siejko et al. | |
| 2004/0106961 A1 | 6/2004 | Siejko et al. | |
| 2004/0133247 A1 | 7/2004 | Stahmann et al. | |
| 2004/0230240 A1 | 11/2004 | Sun et al. | |
| 2004/0255956 A1 | 12/2004 | Vinten-Johansen et al. | |
| 2005/0004476 A1 | 1/2005 | Payvar et al. | |
| 2005/0038345 A1 | 2/2005 | Gorgenberg et al. | |
| 2005/0043675 A1 | 2/2005 | Pastore et al. | |
| 2005/0075673 A1 | 4/2005 | Warkentin et al. | |
| 2005/0090719 A1 | 4/2005 | Scheiner et al. | |
| 2005/0096706 A1 | 5/2005 | Salo | |
| 2005/0131467 A1 | 6/2005 | Boveja | |
| 2005/0137631 A1 | 6/2005 | Yu et al. | |
| 2005/0143779 A1 | 6/2005 | Libbus | |
| 2005/0143780 A1 | 6/2005 | Henry et al. | |
| 2005/0149129 A1 | 7/2005 | Libbus et al. | |
| 2005/0171589 A1 | 8/2005 | Lau et al. | |
| 2005/0197674 A1 | 9/2005 | McCabe et al. | |
| 2005/0261741 A1 | 11/2005 | Libbus et al. | |
| 2005/0283195 A1 | 12/2005 | Pastore et al. | |
| 2005/0288721 A1 | 12/2005 | Girouard et al. | |
| 2006/0020294 A1 | 1/2006 | Brockway et al. | |
| 2006/0030892 A1 | 2/2006 | Kadhiresan et al. | |
| 2006/0116593 A1 | 6/2006 | Zhang et al. | |
| 2006/0136049 A1 | 6/2006 | Rojo | |
| 2006/0149326 A1 | 7/2006 | Prinzen et al. | |
| 2006/0195038 A1 | 8/2006 | Carlson et al. | |
| 2006/0206158 A1 | 9/2006 | Wu et al. | |
| 2006/0241357 A1 | 10/2006 | Chirife | |
| 2006/0241704 A1 | 10/2006 | Shuros et al. | |
| 2006/0247686 A1 | 11/2006 | Girouard et al. | |
| 2006/0247700 A1 | 11/2006 | Jackson | |
| 2006/0253156 A1 | 11/2006 | Pastore et al. | |
| 2006/0259087 A1 | 11/2006 | Baynham et al. | |
| 2006/0259088 A1 | 11/2006 | Pastore et al. | |
| 2006/0271119 A1 | 11/2006 | Ni et al. | |
| 2006/0282000 A1 | 12/2006 | Zhang et al. | |
| 2006/0287684 A1 | 12/2006 | Baynham et al. | |
| 2007/0021789 A1 | 1/2007 | Pastore et al. | |
| 2007/0021790 A1 | 1/2007 | Kieval et al. | |
| 2007/0043393 A1 | 2/2007 | Brockway et al. | |
| 2007/0049835 A1 | 3/2007 | Goode | |
| 2007/0054871 A1 | 3/2007 | Pastore et al. | |
| 2007/0150005 A1 | 6/2007 | Sih et al. | |
| 2007/0150015 A1 | 6/2007 | Zhang et al. | |
| 2007/0162081 A1 | 7/2007 | Yu et al. | |
| 2007/0179392 A1 | 8/2007 | Zhang | |
| 2007/0233192 A1 | 10/2007 | Craig | |
| 2007/0239218 A1 | 10/2007 | Carlson et al. | |
| 2007/0282380 A1 | 12/2007 | Brooke et al. | |
| 2007/0299356 A1 | 12/2007 | Wariar et al. | |
| 2008/0027495 A1 | 1/2008 | Prinzen et al. | |
| 2008/0058661 A1 | 3/2008 | Bardy | |
| 2008/0058881 A1 | 3/2008 | Wagner et al. | |
| 2008/0071315 A1 | 3/2008 | Baynham et al. | |
| 2008/0081354 A1 | 4/2008 | Qu et al. | |
| 2008/0082135 A1 | 4/2008 | Arcot-Krishnamurthy et al. | |
| 2008/0091138 A1 | 4/2008 | Pastore et al. | |

(56) References Cited

U.S. PATENT DOCUMENTS

| | | |
|---|---|---|
| 2008/0132972 A1 | 6/2008 | Shuros et al. |
| 2008/0140141 A1 | 6/2008 | Ben-David et al. |
| 2008/0177156 A1 | 7/2008 | Zhang et al. |
| 2008/0177191 A1 | 7/2008 | Patangay et al. |
| 2008/0177194 A1 | 7/2008 | Zhang et al. |
| 2008/0215105 A1 | 9/2008 | Pastore et al. |
| 2009/0025459 A1 | 1/2009 | Zhang et al. |
| 2009/0048641 A1 | 2/2009 | Libbus |
| 2009/0082781 A1 | 3/2009 | Tran et al. |
| 2009/0124916 A1 | 5/2009 | Sweeney et al. |
| 2009/0192560 A1 | 7/2009 | Arcot-Krishnamurthy et al. |
| 2009/0234401 A1 | 9/2009 | Zielinski et al. |
| 2009/0281591 A1 | 11/2009 | Shuros et al. |
| 2010/0016913 A1 | 1/2010 | Arcot-Krishnamurthy et al. |
| 2010/0016916 A1 | 1/2010 | Arcot-Krishnamurthy et al. |
| 2010/0130913 A1 | 5/2010 | Baynham et al. |
| 2010/0305648 A1 | 12/2010 | Arcot-krishnamurthy et al. |
| 2011/0071584 A1 | 3/2011 | Mokelke et al. |
| 2011/0106197 A1 | 5/2011 | Arcot-Krishnamurthy et al. |
| 2011/0137363 A1 | 6/2011 | Baynham et al. |
| 2011/0144709 A1 | 6/2011 | Baynham et al. |

FOREIGN PATENT DOCUMENTS

| | | |
|---|---|---|
| EP | 1437159 A1 | 7/2004 |
| EP | 1690566 A1 | 8/2006 |
| JP | 10263093 A | 10/1998 |
| WO | WO-95/18649 A1 | 7/1995 |
| WO | WO-00/78391 A1 | 12/2000 |
| WO | WO-0078391 A1 | 12/2000 |
| WO | WO-01/15609 A1 | 3/2001 |
| WO | WO-0128625 | 4/2001 |
| WO | WO-2004/058326 A2 | 7/2004 |
| WO | WO-2006/074189 A1 | 7/2006 |
| WO | WO-2006079010 A1 | 7/2006 |
| WO | WO-2006/115693 A2 | 11/2006 |
| WO | WO-2006/124636 A2 | 11/2006 |
| WO | WO-2006/124729 A2 | 11/2006 |
| WO | WO-2006115693 A3 | 11/2006 |
| WO | WO-2006121842 A2 | 11/2006 |
| WO | WO-2007/133962 A2 | 11/2007 |
| WO | WO-2006/109040 A2 | 9/2008 |

OTHER PUBLICATIONS

"International Application Serial No. PCT/US2008/002799, Written Opinion mailed Oct. 15, 2008", 11 pgs.

"International Application Serial No. PCT/US2008/002799, International Search Report mailed Oct. 15, 2008", 6 pgs.

"U.S. Appl. No. 11/113,828, Final Office Action mailed Jun. 29, 2009", 11 pgs.

"U.S. Appl. No. 11/113,828, Final Office Action mailed Sep. 17, 2008", 10 pgs.

"U.S. Appl. No. 11/113,828, Non-Final Office Action mailed Mar. 5, 2008", 9 pgs.

"U.S. Appl. No. 11/113,828, Non-Final Office Action mailed Dec. 22, 2008", 10 pgs.

"U.S. Appl. No. 11/113,828, Response filed Jan. 28, 2008 to Restriction Requirement mailed Dec. 26, 2007", 7 pgs.

"U.S. Appl. No. 11/113,828, Response filed Mar. 23, 2009 to Non-Final Office Action mailed Dec. 22, 2008", 8 pgs.

"U.S. Appl. No. 11/113,828, Response filed Jun. 5, 2008 to Non-Final Office Action mailed Mar. 5, 2008", 8 pgs.

"U.S. Appl. No. 11/113,828, Response filed Nov. 17, 2008 to Final Office Action mailed Sep. 17, 2008", 11 pgs.

"U.S. Appl. No. 11/113,828, Restriction Requirement mailed Dec. 26, 2007", 6 pgs.

"U.S. Appl. No. 11/129,050, Advisory Action mailed Jul. 14, 2009", 3 pgs.

"U.S. Appl. No. 11/129,050, Final Office Action mailed Apr. 21, 2009", 10 pgs.

"U.S. Appl. No. 11/129,050, Non-Final Office Action mailed Nov. 6, 2008", 7 pgs.

"U.S. Appl. No. 11/129,050, Response filed Feb. 23, 2009 to Non-Final Office Action mailed Nov. 6, 2008", 13 pgs.

"U.S. Appl. No. 11/129,050, Response filed Jun. 22, 2009 to Final Office Action mailed Apr. 21, 2009", 9 pgs.

"U.S. Appl. No. 11/382,489, Restriction Requirement mailed May 6, 2009", 6 pgs.

"U.S. Appl. No. 11/129,050, Advisory Action mailed Jul. 28, 2008", 3 pgs.

"U.S. Appl. No. 11/129,050, Final Office Action mailed May 12, 2008", 8 pgs.

"U.S. Appl. No. 11/129,050, Response filed Jul. 14, 2008 to Final Office Action mailed May 12, 2008", 13 pgs.

"U.S. Appl. No. 11/129,058, Advisory Action mailed Oct. 17, 2007", 3 pgs.

"U.S. Appl. No. 11/129,058, Appeal Brief filed Feb. 8, 2008", 23 pgs.

"U.S. Appl. No. 11/129,058, Examiner's Answer mailed Jun. 18, 2008", 14 pgs.

"U.S. Appl. No. 11/458,286, Notice of Allowance mailed May 28, 2008", 7 pgs.

"International Application Serial No. PCT/US2008/002799, Invitation to Pay Fees and Partial International Search Report mailed Jul. 14, 2008", 7 pgs.

"U.S. Appl. No. 11/030,575 Non Final Office Action mailed Jul. 26, 2006", 11 pgs.

"U.S. Appl. No. 11/030,575 Notice of Allowance mailed Jan. 17, 2007", 10 pgs.

"U.S. Appl. No. 11/030,575 Notice of Allowance mailed Jun. 7, 2007", 10 pgs.

"U.S. Appl. No. 11/030,575 Response filed Oct. 26, 2006 to Non Final Office Action mailed Jul. 26, 2006", 8 pgs.

"U.S. Appl. No. 11/113,828 Non-Final Office Action mailed Mar. 5, 2008", 9 pgs.

"U.S. Appl. No. 11/129,050 Restriction Requirement mailed Aug. 1, 2007", 6 pgs.

"U.S. Appl. No. 11/129,050, Non-Final Office Action mailed Nov. 26, 2007", 7 pgs.

"U.S. Appl. No. 11/129,050, Response filed Feb. 26, 2008 to Non-Final Office Action mailed Nov. 26, 2007", 14 pgs.

"U.S. Appl. No. 11/129,050, Response filed Sep. 28, 2007 to Restriction Requirement mailed Aug. 1, 2007", 11 pgs.

"U.S. Appl. No. 11/129,058 Final Office Action mailed Jul. 9, 2007", 17 pgs.

"U.S. Appl. No. 11/129,058 Non Final office action mailed Jan. 29, 2007", 12 pgs.

"U.S. Appl. No. 11/129,058 Response filed Apr. 30, 2007 to Non Final office action mailed Jan. 29, 2007", 16 pgs.

"U.S. Appl. No. 11/129,058, Response filed Oct. 9, 2007 to Final Office Action mailed Jul. 9, 2007", 14 pgs.

"U.S. Appl. No. 11/151,015 Non Final office action mailed May 21, 2007", 14 pgs.

"U.S. Appl. No. 11/151,015, Response filed Aug. 21, 2007 to Non-Final Office Action mailed May 21, 2007", 9 pgs.

"U.S. Appl. No. 11/151,015 Notice of Allowance mailed Dec. 6, 2007", 6 pgs.

"U.S. Appl. No. 11/458,286, Notice of Allowance mailed Nov. 26, 2007", 7 pgs.

"PCT Application No. PCT/US2006/000125, International Search Report and Written Opinion mailed May 11, 2006", 12 pgs.

"PCT Application No. PCT/US2006/018642, International Search Report and Written Opinion mailed Oct. 24, 2006", 14 pgs.

"PCT Application No. PCT/US2007/068217, International Search Report mailed Oct. 30, 2007", 5 pgs.

"PCT Application No. PCT/US2007/068217, Written Opinion mailed Oct. 30, 2007", 8 pgs.

Airaksinen, K. E., et al., "Antiarrhythmic effect of repeated coronary occlusion during balloon angioplasty", *J Am Coll Cardiol.*, 29(5), (1997),1035-1038.

Amende, I. , "Hemodynamics in ischemia: diastolic phase", *Z. Kardiol.*, 73 Suppl 2, [Article in German With English Abstract], (1984), 127-33.

(56) References Cited

OTHER PUBLICATIONS

Baynham, Tamara C., et al., "Integrated Catheter and Pulse Generator Systems and Methods", U.S. Appl. No. 11/468,875, filed Aug. 31, 2006, 23 Pages.

Dzwonczyk, R., et al., "Myocardial electrical impedance responds to ischemia and reperfusion in humans", *IEEE Transactions on Biomedical Engineering*, 51(12), (2004), 2206-2209.

Girouard, Steven D., "Pulmonary Vein Stent for Treating Atrial Fibrillation", U.S. Appl. No. 60/298,741, filed Jun. 15, 2001, 14 pgs.

Henriques, Jose P., et al., "Outcome of primary angioplasty for acute myocardial infarction during routine duty hours versus during off-hours", *J Am Coll Cardiol*, 41(12), (2003), 2138-2142.

Ishihara, M., et al., "Implications of prodromal angina pectoris in anterior wall acute myocardial infarction: acute angiographic findings and long-term prognosis", *J Am Coll Cardiol.*, 30(4), (1997), 970-975.

Kin, Hajime, et al., "Postconditioning attenuates myocardial ischemia-reperfusion injury by inhibiting events in the early minutes of reperfusion", *Cardiovascular Research*, 62(1), (2004), 74-85.

Kis, A., "Repeated cardiac pacing extends the time during which canine hearts are protected against ischaemia-induced arrhythmias : role of nitric oxide.", *Journal of Molecular and Cellular Cardiology*, 31(6), (1999), 1229-1241.

Kloner, R. A., et al., "Prospective temporal analysis preinfarction angina versus outcome: an ancillary study in TIMI-9B", *Circulation*, 97(11), (1998), 1042-1045.

Koning, M M., "Rapid ventricular pacing produces myocardial protection by nonischemic activation of $K_{ATP}^+$ channels", Circulation, 93(1), (1996), 178-186.

Krayenbühl, H. P., "Hemodynamics in ischemia. Systolic phase", *Z. Kardiol.*, 73 Suppl 2, [Article in German with English Abstract],(1984),119-125.

Makhoul, J., "Linear Prediction: A Tutorial Review", *Proceedings of the IEEE*, 63, (1975), 561-580.

Meier, B., et al., "Coronary Pacing During Percutaneous Transluminal Coronary Angioplasty", *Therapy and Prevention Cardiac Pacing*, 71(3), (1985), 557-561.

Murry, C. E., "Preconditioning with ischemia: a delay of lethal cell injury in ischemic myocardium", *Circulation*, 74(5), (1986),1124-1136.

Ovize, M., et al., "Stretch preconditions canine myocardium.", *Am J Physiol.*, 266(1 Pt 2), (1994), H137-H146.

Panju, A. A., et al., "Is This Patient Having a Myocardial Infarction?", *JAMA*, 280(14), (1998), 1256-1263.

Patangay, Ahilash, et al., "Ischemia Detection Using Heart Sound Timing", U.S. Appl. No. 11/625,003, filed Jan. 19, 2007, 69 Pages.

Prinzen, F. W., "Mapping of regional myocardial strain and work during ventricular pacing: experimental study using magnetic resonance imaging tagging", *Journal of the American College of Cardiology*, 33(6), (1999), 1735-1742.

Rosa, A., et al., "Ectopic Pacing at Physiological Rate Improves Postanoxic Recovery of the Developing Heart", *Am. J. Physiol.—Heart Circ. Physiol.*, 284, (2003), H2384-H2392.

Salerno, D. M., "Seismocardiography for monitoring changes in left ventricular function during ischemia.", *Chest*, 100(4), (1991), 991-993.

Solomon, S. D., et al., "Angina pectoris prior to myocardial infarction protects against subsequent left ventricular remodeling", *J Am Coll Cardiol.*, 43(9), (2004), 1511-1514.

Tavel, M. E., "The Appearance of Gallop Rhythm after Exercise Stress Testing", *Clin. Cardiol.*, vol. 19, (1996),887-891.

Tsang, A., et al., "Postconditioning: a form of "modified reperfusion" protects the myocardium by activating the phosphatidylinositol 3-kinase-Akt pathway", *Circ Res.*, 95(3), Epub Jul. 8, 2004,(Aug. 6, 2004),230-2.

Vanagt, W. Y., et al., "Ventricular Pacing for Improving Myocardial Tolerance to Ischemia, Progress Report on Project Guidant—CARIM", (Oct. 2003),25 pgs.

Vegh, A., et al., "Transient ischaemia induced by rapid cardiac pacing results in myocardial preconditioning", *Cardiovascular Research*, 25(12), (Dec. 1991),1051-3.

Wu, Z.-K., et al., "Ischemic preconditioning suppresses ventricular tachyarrhythmias after myocardial revascularization", *Circulation*, 106(24), (Dec. 10, 2002),3091-3096.

Yang, S. M., et al., "Multiple, brief coronary occlusions during early reperfusion protect rabbit hearts by targeting cell signaling pathways", *Journal of the American College of Cardiology*, 44(5), (Sep. 1, 2004),1103-1110.

Zhao, Z.-Q., et al., "Inhibition of myocardial injury by ischemic postconditioning during reperfusion: comparison with ischemic preconditioning", *Am J Physiol.—Heart Circ Physiol*, 285(2), (2003), H579-H588.

"U.S. Appl. No. 11/129,050, Interview Summary mailed Feb. 11, 2009", 2 pgs.

"U.S. Appl. No. 11/129,050, Notice of Allowance mailed Aug. 24, 2009", 7 pgs.

"U.S. Appl. No. 11/129,050, Notice of Allowance mailed Dec. 2, 2009", 4 pgs.

"U.S. Appl. No. 11/129,050, Notice of Allowance mailed Apr. 1, 2010", 6 pgs.

"U.S. Appl. No. 11/318,263, Non-Final Office Action mailed Aug. 20, 2008", 10 pgs.

"U.S. Appl. No. 11/318,263, Response filed Nov. 20, 2008 to Non Final Office Action mailed Aug. 20, 2008", 12 pgs.

"U.S. Appl. No. 11/318,263, Final Office Action mailed Mar. 17, 2009", 11 pgs.

"U.S. Appl. No. 11/318,263, Response filed Aug. 12, 2009 to Restriction Requirement mailed Jul. 14, 2009", 9 pgs.

"U.S. Appl. No. 11/382,849 Final Office Action mailed Jan. 28, 2010", 8 pgs.

"U.S. Appl. No. 11/382,849, Non-Final Office Action mailed Aug. 31, 2009", 8 pgs.

"U.S. Appl. No. 11/382,849, Response filed Jun. 8, 2009 to Restriction Requirement mailed May 6, 2009", 8 pgs.

"U.S. Appl. No. 11/382,849, Response filed Nov. 30, 2009 to Non Final Office Action mailed Aug. 31, 2009", 11 pgs.

"U.S. Appl. No. 11/382,849, Response filed Apr. 26, 2010 to Final Office Action mailed Jan. 28, 2010", 10 pgs.

"U.S. Appl. No. 11/868,767, Notice of Allowance mailed Mar. 24, 2010", 7 pgs.

"U.S. Appl. No. 11/382,849, Non-Final Office Action mailed May 12, 2010", 5 pages.

"European Application Serial No. 07797336.0, Office Action mailed Feb. 24, 2009", 4 pgs.

"European Application Serial No. 08726356.2, Office Action mailed May 31, 2010", 7 Pgs.

"International Application Serial No. PCT/US2006/017384, International Search Report and Written Opinion mailed Jan. 23, 2007", 12 pgs.

Andersen, H., et al., "Long-term follow-up of patients from a randomised trial of atrial versus ventricular pacing for sick-sinus syndrome", *Lancet*, 350(9086), (Oct. 25, 1997), 1210-6.

Benchimol, A, et al., "Cardiac hemodynamics during stimulation of the right atrium, right ventricle, and left ventricle in normal and abnormal hearts", *Circulation*, 33(6), (Jun. 1966), 933-44.

Grassi, Guido, et al., "Baroreflex and non-baroreflex modulation of vagal cardiac control after myocardial infarction", *Am J Cardiol.*, 84(5), (Sep. 1, 1999), 525-9.

Leclercq, C, et al., "Hemodynamic importance of preserving the normal sequence of ventricular activation in permanent cardiac pacing", *Am Heart J.*, 129(6), (Jun. 1995), 1133-41.

Loukogeorgakis, S. P., et al., "Remote ischemic preconditioning provides early and late protection against endothelial ischemia-reperfusion injury in humans: role of the autonomic nervous system.", *J Am Coll Cardiol.*, 46(3), (Aug. 2, 2005), 450-6.

Rosenqvist, M, et al., "The effect of ventricular activation sequence on cardiac performance during pacing", *Pacing and Electrophysiology*, 19(9), (1996), 1279-1286.

"U.S. Appl. No. 11/129,050, Notice of Allowance mailed Jul. 16, 2010", 4 pgs.

(56) References Cited

OTHER PUBLICATIONS

"U.S. Appl. No. 11/382,849, Response filed Aug. 2, 2010 to Non Final Office Action mailed May 12, 2010", 7 pgs.
"Australian Application Serial No. 2008223498, First Examiner Report mailed Aug. 16, 2010", 3 pgs.
"European Application Serial No. 07797336.0, Response filed Jul. 6, 2009 to Communication mailed Feb. 24, 2009", 20 pgs.
"European Application Serial No. 08726356.2, Response filed Aug. 27, 2010 to Communication dated May 31, 2010", 14 pgs.
"U.S. Appl. No. 11/129,050, Notice of Allowance mailed Nov 1, 2010", 6 pgs.
"U.S. Appl. No. 11/382,849, Notice of Allowance mailed Oct. 15, 2010", 6 pgs.
"U.S. Appl. No. 11/868,767, Notice of Allowance mailed Sep. 17, 2010", 4 pgs.
"Japanese Application Serial No. 2009-552705, Amendment filed Oct. 21, 2009", (w/ English Translation), 43 pgs.
US 7,877,143, 1/2011, Frits, P, et al. (withdrawn).
"U.S. Appl. No. 11/868,767, Notice of Allowance mailed Mar. 3, 2011", 5 pgs.
"Australia Application Serial No. 2008223498, Response filed May 25, 2011 to First Examiner Report mailed Aug. 16, 2010", 21 pgs.
"Japanese Application Serial No. 2009-552705, Response filed Mar. 6, 2012 to Office Action mailed Dec. 6, 2011", (w/ English Translation of Amended Claims), 11 pgs.
"Japanese Application Serial No. 2009-552705, Office Action mailed Dec. 6, 2011", 12 pgs.
"U.S. Appl. No. 12/770,351, Non Final Office Action mailed Oct. 11, 2012", 13 pgs.
"U.S. Appl. No. 13/019,888, Non Final Office Action mailed Jun. 29, 2012", 9 pgs.
"U.S. Appl. No. 13/019,888, Notice of Allowance mailed Nov. 6, 2012", 8 pgs.
"U.S. Appl. No. 13/019,888, Response filed Sep. 28, 2012 to Non Final Office Action mailed Jun. 29, 2012", 10 pgs.
"U.S. Appl. No. 13/019,888, Response to Restriction Requirement mailed Apr. 2, 2012", 8 pgs.
"U.S. Appl. No. 13/019,888, Restriction Requirement mailed Apr. 2, 2012", 5 pgs.
"U.S. Appl. No. 13/029,631, Non Final Office Action mailed Apr. 12, 2012", 7 pgs.
"U.S. Appl. No. 13/029,631, Notice of Allowance mailed Aug. 24, 2012", 7 pgs.
"U.S. Appl. No. 13/029,631, Response filed Jul. 10, 2012 to Non Final Office Action mailed Apr. 12, 2012", 8 pgs.
"Chinese Application Serial No. 200880007463.3, Office Action mailed Mar. 6, 2012", (w/ English Translation), 21 pgs.
"Chinese Application Serial No. 200880007463.3, Response filed Jul. 23, 2012 to Office Action mailed Mar. 14, 2012", (English Translation of Amended Claims), 5 pgs.
"European Application Serial No. 08726356.2, Examination Notification Art. 94(3) mailed Aug. 22, 2012", 5 pgs.
"Japanese Application Serial No. 2009-552705, Office Action mailed Apr. 19, 2012", (w/ English Translation), 7 pgs.
"U.S. Appl. No. 13/721,796, Non Final Office Action mailed May 3, 2013", 7 pgs.
"European Application Serial No. 08726356.2, Response filed Dec. 19, 2012 to Examination Notification Art. 94(3) mailed Aug. 22, 2012", 14 pgs.

\* cited by examiner

METHOD AND APPARATUS FOR CLOSED-LOOP INTERMITTENT CARDIAC STRESS AUGMENTATION PACING

CROSS-REFERENCE TO RELATED APPLICATIONS

This application is related to co-pending, commonly assigned, U.S. patent application Ser. No. 11/129,050, entitled "METHOD AND APPARATUS FOR CARDIAC PROTECTION PACING," filed on May 13, 2005 and U.S. patent application Ser. No. 11/030,575, entitled "INTERMITTENT STRESS AUGMENTATION PACING FOR CARDIOPROTECTIVE EFFECT," filed on Jan. 6, 2005, which are hereby incorporated by reference in their entirety.

TECHNICAL FIELD

This document relates generally to cardiac rhythm management (CRM) systems and particularly a system providing for feedback controlled cardiac pacing that intermittently creates or augments stress in the heart.

BACKGROUND

The heart is the center of a person's circulatory system. It includes an electro-mechanical system performing two major pumping functions. The left portions of the heart draw oxygenated blood from the lungs and pump it to the organs of the body to provide the organs with their metabolic needs for oxygen. The right portions of the heart draw deoxygenated blood from the organs and pump it into the lungs where the blood gets oxygenated. The pumping functions are accomplished by contractions of the myocardium (heart muscles). In a normal heart, the sinoatrial node, the heart's natural pacemaker, generates electrical impulses, known as action potentials, that propagate through an electrical conduction system to various regions of the heart to excite myocardial tissues in these regions. Coordinated delays in the propagations of the action potentials in a normal electrical conduction system cause the various regions of the heart to contract in synchrony such that the pumping functions are performed efficiently.

A blocked or otherwise damaged electrical conduction system causes irregular contractions of the myocardium, a condition generally known as arrhythmia. Arrhythmia reduces the heart's pumping efficiency and hence, diminishes the blood flow to the body. A deteriorated myocardium has decreased contractility, also resulting in diminished blood flow. A heart failure patient usually suffers from both a damaged electrical conduction system and a deteriorated myocardium. The diminished blood flow results in insufficient blood supply to various body organs, preventing these organs to function properly and causing various symptoms.

Without timely and effective treatment, a cardiac disorder may develop to an extent that significantly lowers the patient's quality of life and threats the patient's life. For example, heart failure may progress rapidly, with continuously deteriorating cardiac conditions and hemodynamic performance that could lead to inability to carry out daily activities and death. For these and other reasons, there is a need for controlling the progression of cardiac disorders, such as heart failure.

SUMMARY

A cardiac pacing system controls the progression of a cardiac disorder such as heart failure by delivering cardiac pacing to create or augment regional stress in the heart. The cardiac pacing is delivered intermittently, such as on a periodic basis, according to a cardiac stress augmentation pacing sequence that includes alternating pacing and non-pacing periods. One or more physiological signals are monitored for closed-loop control of the cardiac pacing using baseline characteristics of the cardiac disorder, acute cardiac stress created by the cardiac pacing, and/or risk associated with the cardiac pacing.

In one embodiment, a cardiac rhythm management (CRM) system includes one or more sensors, a signal analyzer, a pacing circuit, and a pacing controller. The one or more sensors sense one or more physiological signals. The signal analyzer produces one or more physiological parameters indicative of progression of a cardiac disorder and a level of acute cardiac stress using the one or more physiological signals. The pacing circuit delivers cardiac pacing pulses. The pacing controller provides feedback control of the delivery of the cardiac pacing pulses using the one or more physiological parameters. The pacing controller includes a stress augmentation pacing initiator, a stress augmentation pacing timer, and a pacing parameter adjuster. The stress augmentation pacing initiator initiates a cardiac stress augmentation pacing sequence. The cardiac stress augmentation pacing sequence has a sequence duration and includes alternating pacing and non-pacing periods. The pacing periods each have a pacing duration during which a plurality of the cardiac pacing pulses is delivered. The non-pacing periods each have a non-pacing duration during which none of the cardiac pacing pulses is delivered. The stress augmentation pacing timer times the cardiac stress augmentation pacing sequence. The pacing parameter adjuster adjusts one or more pacing parameters for the cardiac stress augmentation pacing sequence using the one or more physiological parameters.

In one embodiment, a method for operating a CRM system is provided. One or more physiological signals are sensed. One or more physiological parameters indicative of progression of a cardiac disorder and a level of acute cardiac stress are produced using the one or more physiological signals. Cardiac pacing pulses are delivered according to a cardiac stress augmentation pacing sequence. The cardiac stress augmentation pacing sequence has a sequence duration and includes alternating pacing and non-pacing periods. The pacing periods each have a pacing duration during which a plurality of the cardiac pacing pulses is delivered. The non-pacing periods each have a non-pacing duration during which none of the cardiac pacing pulses is delivered. One or more pacing parameters for the cardiac stress augmentation pacing sequence are adjusted using the one or more physiological parameters.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof. The scope of the present invention is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. References to "an", "one", or "various" embodiments in this disclosure are not necessarily to the same embodiment, and such references contemplate more than one embodiment. The following detailed description provides examples, and the scope of the present invention is defined by the appended claims and their legal equivalents.

This document discusses a pacing system including an implantable medical device that controls progression of a cardiac disorder by intermittently delivering pacing pulses in a way that creates or augments regional stress in the heart. In one embodiment, the pacing system controls progression of heart failure by intermittently delivering pacing pulses to increase the degree of ventricular asynchrony. The pacing pulses are delivered according to a cardiac stress augmentation pacing sequence that includes alternating pacing and non-pacing periods. The pacing periods each have a pacing duration during which pacing pulses are delivered. The non-pacing periods each have a non-pacing duration during which no pacing pulse is delivered. The cardiac stress augmentation pacing sequence is initiated according to a predetermined schedule, such as on an approximately periodic basis. Baseline characteristics of the cardiac disorder are chronically analyzed to provide for closed-loop control of the pacing parameters to achieve a desirable level of control on the progression of the cardiac disorder. Acute cardiac stress is analyzed during the cardiac stress augmentation pacing sequence to provide for closed-loop control of the pacing parameters for an adequate level of acute cardiac stress, which is used to slow the progression of the cardiac disorder. Risk associated with pacing is analyzed during the cardiac stress augmentation pacing sequence to ensure that the pacing does not cause intolerable change in the cardiac function or hemodynamic performance.

Figure 1:
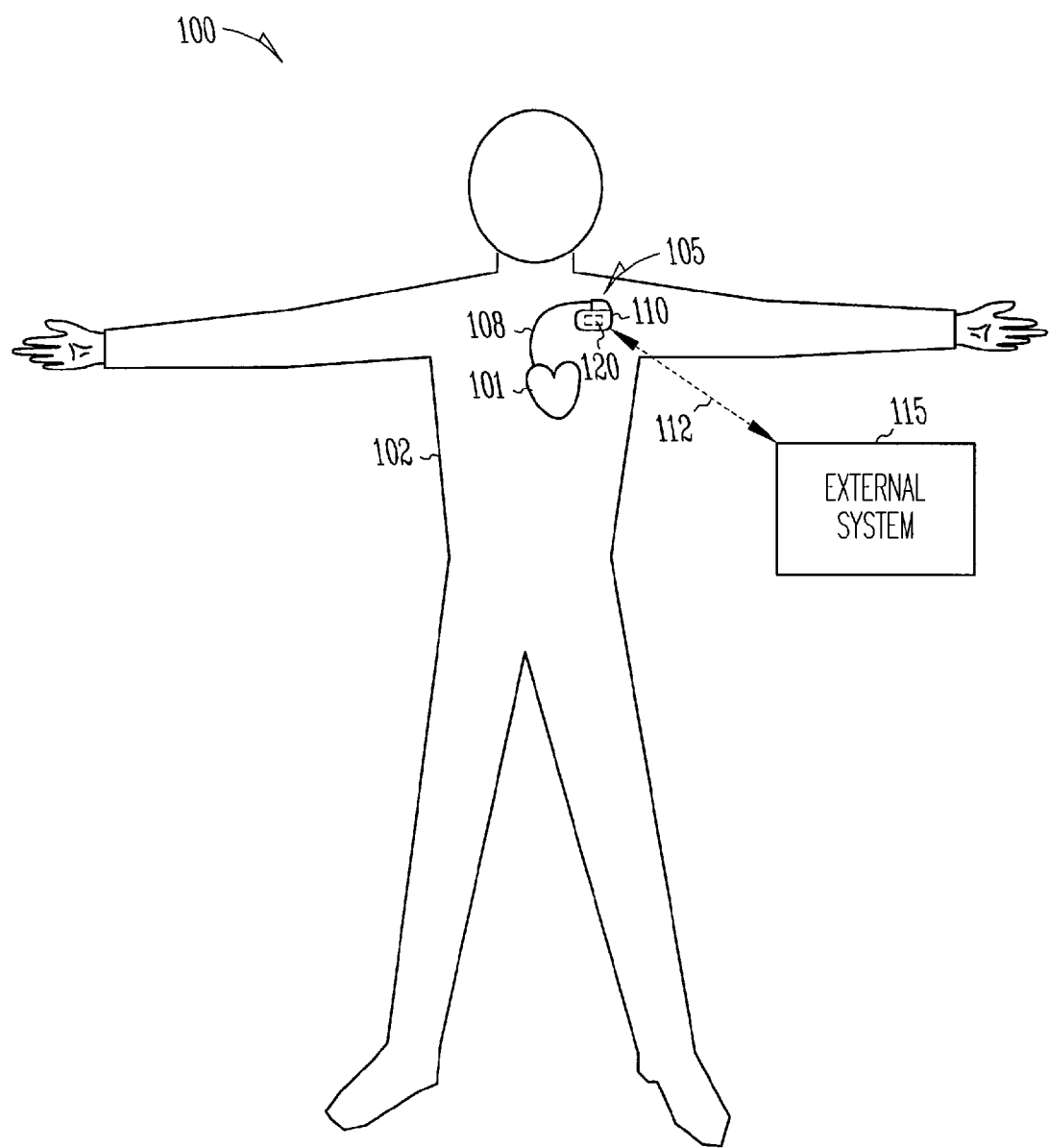
FIG. 1 is an illustration of one embodiment of a CRM system and portions of the environment in which the CRM system operates.

FIG. 1 is an illustration of an embodiment of a cardiac rhythm management (CRM) system 100 and portions of an environment in which system 100 is used. System 100 includes an implantable system 105, an external system 115, and a telemetry link 112 providing for communication between implantable system 105 and external system 115.

Implantable system 105 includes, among other things, implantable medical device 110 and lead system 108. In various embodiments, implantable medical device 110 is an implantable CRM device including one or more of a pacemaker, a cardioverter/defibrillator, a cardiac resynchronization therapy (CRT) device, a cardiac remodeling control therapy (RCT) device, a neurostimulator, a drug delivery device or a drug delivery controller, and a biological therapy device. As illustrated in FIG. 1, implantable medical device 110 is implanted in a body 102. In various embodiments, lead system 108 includes leads for sensing physiological signals and delivering pacing pulses, cardioversion/defibrillation shocks, neurostimulation, pharmaceutical agents, biological agents, and/or other types of energy or substance for treating cardiac disorders. In various embodiments, electrodes placed in a heart 101 or other portions of body 102 are used to sense physiological signals and deliver pacing pulses, cardioversion/defibrillation shocks, neurostimulation, pharmaceutical agents, biological agents, and/or other types of energy or substance for treating cardiac disorders. In one embodiment, lead system 108 includes one or more pacing-sensing leads each including at least one electrode placed in or on heart 101 for sensing one or more electrograms and/or delivering pacing pulses. In a specific embodiment, lead system 108 allows pacing pulses to be delivered to multiple atrial and ventricular sites.

Implantable medical device 110 includes an intermittent pacing system 120. Intermittent pacing system 120 includes sensing and pacing circuitry for delivering intermittent cardiac pacing to heart 101 according to a cardiac stress augmentation pacing sequence. In one embodiment, in addition to the intermittent cardiac pacing, implantable medical device 110 also delivers one or more other cardiac pacing therapies, such a bardycardia pacing therapy, CRT, and RCT. If another pacing therapy is being delivered when the intermittent cardiac pacing is to be delivered, that pacing therapy is temporarily suspended to allow the delivery of the intermittent cardiac pacing and resumed upon completion of the cardiac protection pacing sequence. In one embodiment, implantable medical device 110 controls the delivery of one or more of other therapies such as neurostimulation therapy, drug therapy, and biologic therapy in coordination with the intermittent cardiac pacing.

Implantable medical device 110 includes a hermetically sealed can to house electronic circuitry that performs sensing and therapeutic functions. In one embodiment, intermittent pacing system 120 is housed within the hermetically sealed can. In another embodiment, intermittent pacing system 120 includes internal components housed within hermetically sealed can and external components located external to the hermetically sealed can but communicatively coupled to the internal components.

External system 115 allows a user such as a physician or other caregiver or a patient to control the operation of implantable medical device 110 and obtain information acquired by implantable medical device 110. In one embodiment, external system 115 includes a programmer communicating with implantable medical device 110 bi-directionally via telemetry link 112. In another embodiment, external system 115 is a patient management system including an external device communicating with a remote device through a telecommunication network. The external device is within the vicinity of implantable medical device 110 and communicates with implantable medical device 110 bi-directionally via telemetry link 112. The remote device allows the user to monitor and treat a patient from a distant location.

Telemetry link 112 provides for data transmission from implantable medical device 110 to external system 115. This includes, for example, transmitting realtime physiological data acquired by implantable medical device 110, extracting physiological data acquired by and stored in implantable medical device 110, extracting therapy history data stored in implantable medical device 110, and extracting data indicating an operational status of implantable medical device 110 (e.g., battery status and lead impedance). Telemetry link 112 also provides for data transmission from external system 115 to implantable medical device 110. This includes, for example, programming implantable medical device 110 to acquire physiological data, programming implantable medical device 110 to perform at least one self-diagnostic test (such as for a device operational status), and programming implantable medical device 110 to deliver one or more therapies.

Figure 2:
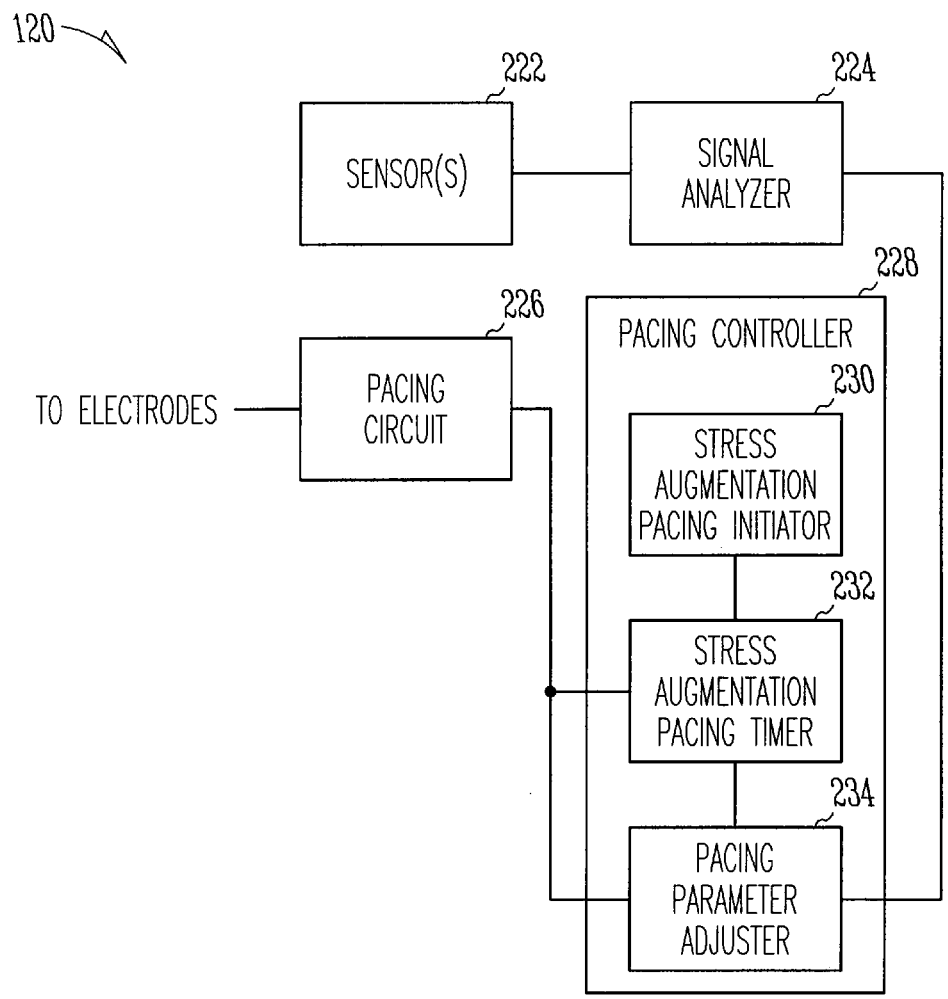
FIG. 2 is a block diagram illustrating an embodiment of an intermittent pacing system of the CRM system.

FIG. 2 is a block diagram illustrating an embodiment of intermittent pacing system 120, which includes one or more sensors 222, a signal analyzer 224, a pacing circuit 226, and a pacing controller 228. Sensor(s) 222 sense one or more physiological signals. Signal analyzer 224 produces one or more physiological parameters indicative of progression of a cardiac disorder and a level of acute cardiac stress using the one or more physiological signals. Pacing circuit 226 delivers pacing pulses to heart 101 through one or more electrodes. Pacing controller 228 controls the delivery of the pacing pulses and includes a stress augmentation pacing initiator 230, a stress augmentation pacing timer 232, and a pacing parameter adjuster 234. The stress augmentation pacing initiator initiates the cardiac stress augmentation pacing sequence, which has a sequence duration and includes alternating pacing and non-pacing periods. The pacing periods each have a pacing duration during which a plurality of the pacing pulses is delivered. The non-pacing periods each have a non-pacing duration during which no pacing pulse is delivered. Stress augmentation pacing timer 232 times the cardiac stress augmentation pacing sequences. The pacing parameter adjuster adjusts one or more pacing parameters for the cardiac stress augmentation pacing sequence using the one or more physiological parameters produced by signal analyzer 224.

Figure 3:
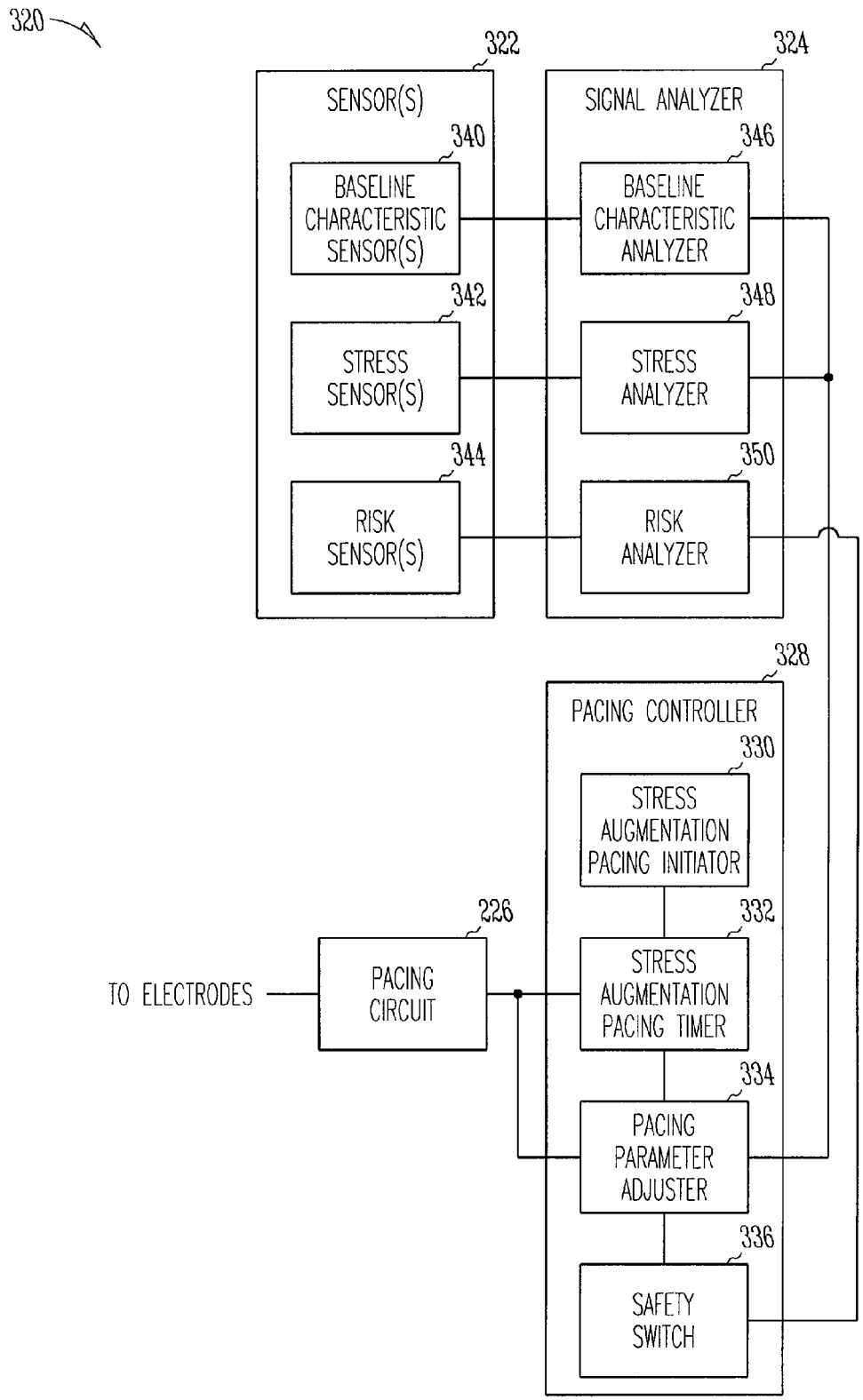
FIG. 3 is a block diagram illustrating a specific embodiment of the intermittent pacing system.

FIG. 3 is a block diagram illustrating an embodiment of an intermittent pacing system 320, which is a specific embodiment of intermittent pacing system 120. Intermittent pacing system 320 includes one or more sensors 322, a signal analyzer 324, pacing circuit 226, and a pacing controller 328. In one embodiment, intermittent pacing system 320 is housed within the hermetically sealed can of implantable medical device 110. In another embodiment, intermittent pacing system 320 is distributed within and external to the hermetically sealed can. For example, signal analyzer 324, pacing circuit 226, and pacing controller 328 are housed within the hermetically sealed can, while at least one sensor of sensor(s) 322 is external to the hermetically sealed can and communicatively coupled to signal analyzer 324.

Sensor(s) 322 sense one or more physiological signals. Using the one or more physiological signals, signal analyzer 324 produces one or more physiological parameters for pacing controller 328 to adjust pacing parameters for the cardiac stress augmentation pacing sequence using feedback control. The one or more physiological parameters indicate one or more of progression of a cardiac disorder, a level of acute cardiac stress, and a degree of cardiac risk associated with cardiac stress. In one embodiment, signal analyzer 324 produces one or more physiological parameters indicative of one of progression of the cardiac disorder and the level of acute cardiac stress. In another embodiment, signal analyzer 324 produces one or more physiological parameters indicative of both the progression of the cardiac disorder and the level of acute cardiac stress. In another embodiment, in addition to the one or more physiological parameters indicative of progression of the cardiac disorder and/or the level of acute cardiac stress, signal analyzer 324 also produces the degree of cardiac risk associated with cardiac stress.

In the illustrated embodiment, sensor(s) 322 include one or more baseline characteristic sensors 340, one or more stress sensors 342, and one or more risk sensors 344. Signal analyzer 324 includes a baseline characteristic analyzer 346, a stress analyzer 348, and a risk analyzer 350. In various other embodiments, sensor(s) 322 include any one or more of baseline characteristic sensor(s) 340, stress sensor(s) 342, and risk sensor(s) 344, and signal analyzer 324 includes the corresponding one or more of baseline characteristic analyzer 346, stress analyzer 348, and risk analyzer 350. Baseline characteristic sensor(s) 322 sense one or more baseline characteristic signals indicative of progression of the cardiac disorder. An example of the cardiac disorder is heart failure. Baseline characteristic analyzer 346 produces one or more baseline characteristic parameters indicative of the progression of the cardiac disorder using the one or more baseline characteristic signals. In one embodiment, baseline characteristic analyzer 346 produces a trend for selected one or more baseline characteristic parameters, such as on a periodic basis. Stress sensor(s) 342 sense one or more stress signals indicative of the level of acute cardiac stress. Stress analyzer 348 produces one or more stress parameters indicative of the level of acute cardiac stress using one or more stress signals. Risk sensor(s) 344 sense one or more risk signals indicative of the degree of cardiac risk associated with cardiac stress. Risk analyzer 350 produces one or more risk parameters indicative of cardiac risk using the one or more risk signals. In one embodiment, one or more sensors each function as two or more of a baseline characteristic sensor 340, a stress sensor 342, and a risk sensor 344.

Pacing controller 328 is a specific embodiment of pacing controller 228 and controls the delivery of the pacing pulses. Pacing controller 328 includes a stress augmentation pacing initiator 330, a stress augmentation pacing timer 332, a pacing parameter adjuster 334, and a safety switch 336.

Stress augmentation pacing initiator 330 initiates the cardiac stress augmentation pacing sequence. The cardiac stress augmentation pacing sequence has a sequence duration and includes alternating pacing and non-pacing periods. The pacing periods each have a pacing duration during which a plurality of the pacing pulses is delivered. The non-pacing periods each have a non-pacing duration during which none of the pacing pulses is delivered. The pacing parameters for the cardiac stress augmentation pacing sequence are selected to acutely increase a cardiac regional stress. In one embodiment, cardiac stress augmentation pacing sequence is a cardiac dyssynchronization pacing sequence for acutely increasing the degree of cardiac asynchrony in a heart failure patient intermittently, such as for a short period of time on an approximately periodic basis. In one embodiment, stress augmentation pacing initiator 330 initiates the cardiac stress augmentation pacing sequence according to a cardiac stress augmentation pacing schedule, such as on a periodic basis. In another embodiment, stress augmentation pacing initiator 330 initiates the cardiac stress augmentation pacing sequence using the cardiac stress augmentation pacing schedule and one or more physiological signals sensed by sensor(s) 322. Examples of such one or more physiological signals include an activity signal indicative of the patient's gross activity level, a posture signal indicative of the patient's posture, a respiratory signal indicative of the patient's respiratory pattern, and a cardiac signal indicative of the patient's heart rate. Using such one or more physiological signals allows stress augmentation pacing initiator 330 to initiate the cardiac stress augmentation pacing sequence while the patient is in a state of resting or low metabolic demand, when the cardiac stress augmentation pacing sequence is to be initiated according to the cardiac stress augmentation pacing schedule.

Cardiac stress augmentation pacing timer 332 times the cardiac stress augmentation pacing sequence once initiated by stress augmentation pacing initiator 330. An example of timing of the cardiac stress augmentation pacing sequence illustrated in FIG. 9.

Pacing parameter adjuster 334 adjusts one or more pacing parameters for the cardiac stress augmentation pacing sequence using one or more physiological parameters produced by signal analyzer 324. Examples of the one or more pacing parameters includes pacing mode, atrioventricular (AV) delay, interventricular (IV) delay, pacing sites, the cardiac stress augmentation pacing period (at which the cardiac stress augmentation pacing sequence is initiated), the sequence duration (or number of pacing periods during the cardiac stress augmentation pacing sequence), the pacing duration, and the non-pacing duration. In one embodiment, one or more AV delays and/or one or more IV delays are adjusted to increase the degree of cardiac asynchrony for the cardiac dyssynchronization pacing sequence.

In one embodiment, pacing parameter adjuster 334 adjusts the one or more pacing parameters to slow the progression of the cardiac disorder using the one or more baseline characteristic parameters produced by baseline characteristic analyzer 346. If the one or more baseline characteristic parameters indicate a slowed progression of the cardiac disorder (i.e., the intended result), pacing parameter adjuster 334 increases the duration and/or level of augmentation of the acute cardiac stress until the progression of the cardiac disorder is satisfactorily controlled. If the one or more baseline characteristic parameters indicate an accelerated progression of the cardiac disorder (i.e., an unintended and potentially harmful result), pacing parameter adjuster 334 decreases the duration and/or level of augmentation of the acute cardiac stress until the progression of the cardiac disorder is slowed. In one embodiment, pacing parameter adjuster 334 adjusts the pacing parameters using the one or more stress parameters produced by stress analyzer 348, such that the one or more stress parameters approaches a target value region specified with one or more values of the one or more stress parameters.

Safety switch 336 stops the cardiac stress augmentation pacing sequence if the one or more risk parameters produced by risk analyzer 350 fall within a predetermined risk zone defined by one or more threshold values. For example, if the one or more risk parameters indicate that the pacing has elevated the acute cardiac stress to a level that is considered potentially unsafe for the patient during the cardiac stress augmentation pacing sequence, safety switch 335 stops the cardiac stress augmentation pacing sequence.

Figure 4:
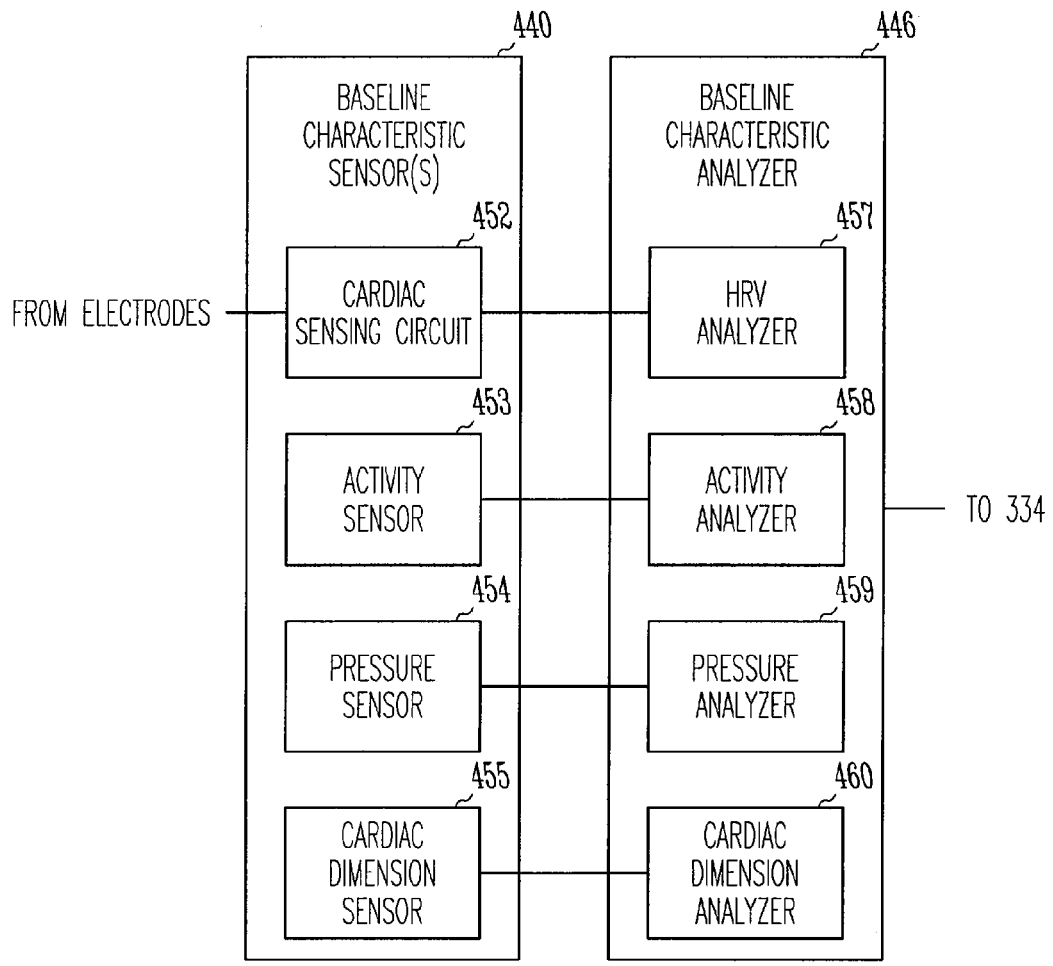
FIG. 4 is a block diagram illustrating an embodiment of baseline characteristic sensor(s) and analyzer of the intermittent pacing system.

FIG. 4 is a block diagram illustrating an embodiment of a baseline characteristic sensor(s) 440, as a specific embodiment of baseline characteristic sensor(s) 340, and a baseline characteristic analyzer 446, as a specific embodiment of baseline characteristic analyzer 346. In the illustrated embodiment, baseline characteristic sensor(s) 440 include a cardiac sensing circuit 452, an activity sensor 453, a pressure sensor 454, and a cardiac dimension sensor 455, and baseline characteristic analyzer 446 includes a heart rate variability (HRV) analyzer 457, an activity analyzer 458, a pressure analyzer 459, and a cardiac dimension analyzer 460. The cardiac disorder for which the baseline characteristics are analyzed is heart failure. In other embodiments, baseline characteristic sensor(s) 440 include any one or more of cardiac sensing circuit 452, activity sensor 453, pressure sensor 454, and cardiac dimension sensor 455, and baseline characteristic analyzer 446 includes the corresponding one or more of HRV analyzer 457, activity analyzer 458, pressure analyzer 459, and cardiac dimension analyzer 460, depending on, for example, sensor availability and/or the desirable feedback control algorithm controlling the pacing parameters. Cardiac sensing circuit 452, activity sensor 453, pressure sensor 454, and cardiac dimension sensor 455 are illustrated in FIG. 4 and discussed as specific examples, and in various embodiments, baseline characteristic sensor(s) 440 include any sensor(s) capable of sensing signal(s) indicative of progression of the cardiac disorder.

Cardiac sensing circuit 452 senses one or more cardiac signals using electrodes such as electrodes on lead system 108. HRV analyzer 457 produces one or more HRV parameters using the one or more cardiac signals. HRV is the beat-to-beat variance in cardiac cycle length over a period of time. An "HRV parameter" as used in this document includes any parameter being a measure of the HRV, including any qualitative expression of the beat-to-beat variance in cardiac cycle length over a period of time. In one embodiment, the HRV parameter is the time differences between successive cardiac cycle lengths averaged over a predetermined period of time. In a specific embodiment, the cardiac cycle lengths are ventricular cycle lengths, i.e., V-V intervals (R-R intervals), which are time intervals between successive ventricular depolarizations (R waves). In another specific embodiment, the cardiac cycle lengths are atrial cycle lengths, i.e., A-A intervals (P-P intervals), which are time intervals between successive atrial depolarizations (P waves). In one embodiment, the one or more HRV parameters produced by HRV analyzer 457 include a Standard Deviation of Averages of Normal-to-Normal intervals (SDANN). Normal-to-Normal intervals refer to R-R intervals during a normal sinus rhythm. To compute SDANN, R-R intervals are measured and averaged over a first time period. The standard deviation of the averaged R-R intervals is computed for a second time period that includes multiple first time periods. In one embodiment, measured R-R intervals are averaged over five-minute periods for 24 hours (i.e., 288 five-minute periods). The SDANN is the standard deviation of five-minute mean R-R intervals computed for the 24-hour period. In another embodiment, the one or more HRV parameters produced by HRV analyzer 457 include an HRV footprint. The HRV footprint refers to a histogram of the HRV plotted against heart rate. The time difference between successive R-R intervals are determined for a period of time and plotted versus the heart rate measured over that period of time. The SDANN and the HRV footprint are examples of HRV parameters used in the closed-loop system that modulates cardiac therapies according to the baseline characteristics that indicates the progression of the patient's cardiac disorder. One of ordinary skill in the art will understand, upon reading and comprehending this document, that other parameters capable of representing or indicating the HRV can be used as the HRV, according to the present subject matter.

Activity sensor 453 senses an activity signal. One example of activity sensor 453 includes an accelerometer. Activity analyzer 458 produces an activity level parameter using the activity signal. In one embodiment, activity analyzer 458 produces an activity log indicative of a frequency at which the activity level exceeds a predetermined threshold. The activity log is indicative of therapy efficacy and patient well-being.

Pressure sensor 454 senses a blood pressure signal. Pressure analyzer 459 produces a cardiac function parameter using the blood pressure signal. In one embodiment, the cardiac function parameter is a systolic blood pressure, which is an indication of cardiac function.

Cardiac dimension sensor 455 senses one or more signals indicative of cardiac dimensions. Examples of cardiac dimension sensor 455 include ultrasonic transducers and impedance sensors. Cardiac dimension analyzer 460 produces one or more cardiac size parameters using the one or more signals indicative of cardiac dimensions. The one or more cardiac size parameters indicate one or more of cardiac chamber diameter, cardiac wall thickness, and cardiac chamber volume. Examples of cardiac dimension sensing using ultrasonic transducer are discussed in U.S. patent application Ser. No. 11/539,939, entitled "METHOD AND APPARATUS FOR CONTROLLING CARDIAC THERAPY USING ULTRASOUND TRANSDUCER", filed Oct. 10, 2006, assigned to Cardiac Pacemakers, Inc., which is hereby incorporated by reference in its entirety. Examples of cardiac dimension sensing using impedance sensing are discussed in U.S. Pat. No. 6,278,894, entitled "MULTI-SITE IMPEDANCE SENSOR USING CORONARY SINUS/VEIN ELECTRODES", assigned to Cardiac Pacemakers, Inc., which is hereby incorporated by reference in its entirety.

Figure 5:
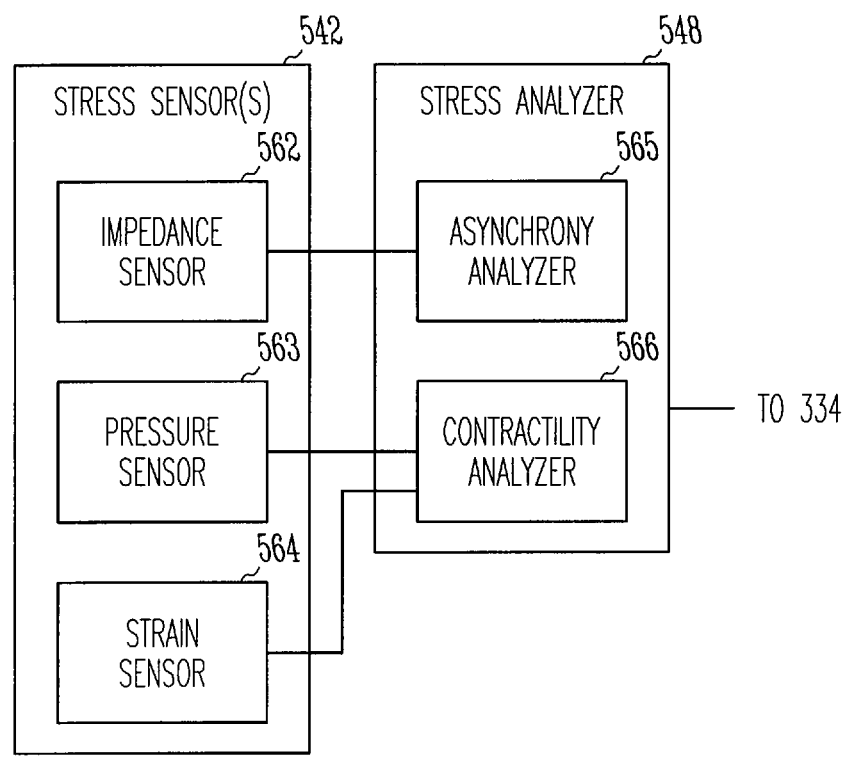
FIG. 5 is a block diagram illustrating an embodiment of stress sensor(s) and analyzer of the intermittent pacing system.

FIG. 5 is a block diagram illustrating an embodiment of stress sensor(s) 542, as a specific embodiment of stress sensor(s) 342, and a stress analyzer 548, as a specific embodiment of stress analyzer 348. In the illustrated embodiment, stress sensor(s) 542 include an impedance sensor 562, a pressure sensor 563 and a strain sensor 564, and stress analyzer 548 includes an asynchrony analyzer 565 and a contractility analyzer 566. In other embodiments, stress sensor(s) 542 include any one or more of impedance sensor 562, pressure sensor 563, and strain sensor 564, and stress analyzer 548 includes any one or both of asynchrony analyzer 565 and contractility analyzer 566. Impedance sensor 562, pressure sensor 563, and strain sensor 564 are illustrated in FIG. 5 and discussed as specific examples, and in various embodiments, stress sensor(s) 542 include any sensor(s) capable of sensing signal(s) indicative cardiac stress.

Impedance sensor 562 senses one or more impedance signals. Asynchrony analyzer 565 produces an asynchrony parameter indicative of a degree of cardiac asynchrony using the one or more impedance signals. In one embodiment, impedance sensor 562 and cardiac dimension sensor 455 include the same impedance sensor.

Pressure sensor 563 senses a blood pressure signal. Contractility analyzer 566 produces a contractility parameter being a measure of cardiac contractility using the blood pressure signal. One example of the contractility parameter is the positive rate of left ventricular pressure change during systole (LV+dp/dt). In one embodiment, pressure sensors 563 and 454 include the same pressure sensor.

Strain sensor 564 senses a strain signal indicative of cardiac contractility. In one embodiment, strain sensor 564 is used as an alternative or an addition to pressure sensor 563 to sense a signal indicative of the cardiac contractility. Contractility analyzer 566 produces a contractility parameter being a measure of cardiac contractility using one or both of the blood pressure signal and the strain signal.

Figure 6:
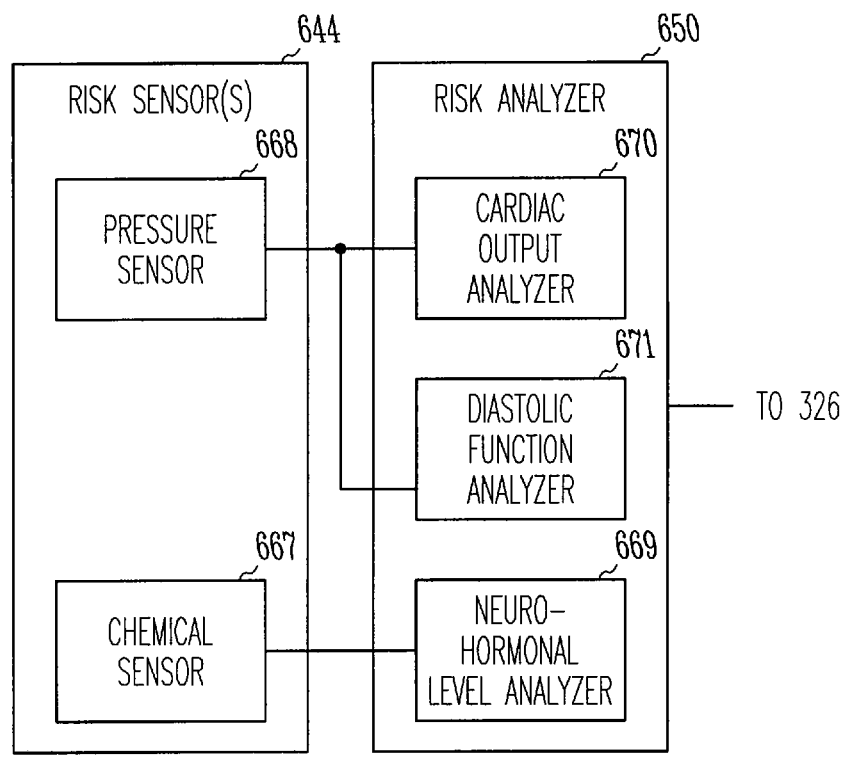
FIG. 6 is a block diagram illustrating an embodiment of risk sensor(s) and analyzer of the intermittent pacing system.

FIG. 6 is a block diagram illustrating an embodiment of risk sensor(s) 644, as a specific embodiment of risk sensor(s) 344, and a risk analyzer 650, as a specific embodiment of risk analyzer 350. In the illustrated embodiment, risk sensor(s) 644 includes a pressure sensor 668 and a chemical sensor 667, and risk analyzer 650 includes a cardiac output analyzer 670, a diastolic function analyzer 671, and a neurohormonal level analyzer 669. In other embodiments, risk sensor(s) 644 includes any one or both of pressure sensor 668 and chemical sensor 667, and risk analyzer 650 includes any one or more of cardiac output analyzer 670, diastolic function analyzer 671, and neurohormonal level analyzer 669. Pressure sensor 668 and chemical sensor 667 are illustrated in FIG. 6 and discussed as a specific examples, and in various embodiments, risk sensor(s) 644 include any sensor(s) capable of sensing signal(s) indicative a degree of cardiac risk.

Pressure sensor 668 senses a blood pressure signal. Cardiac output analyzer 670 produces a systolic blood pressure, which indicates cardiac output, using the blood pressure signal. Diastolic function analyzer 672 produces a diastolic blood pressure, which indicates diastolic function, using the blood pressure signal. In one embodiment, pressure sensors 668, 563, and 454 include the same pressure sensor.

Chemical sensor 667 senses a signal indicative of a neurohormonal level, such as the level of catecholamines within the blood. Neurohormonal level analyzer 669 produces a neurohormonal level parameter using the signal indicative of the neurohormonal level.

Figure 7:
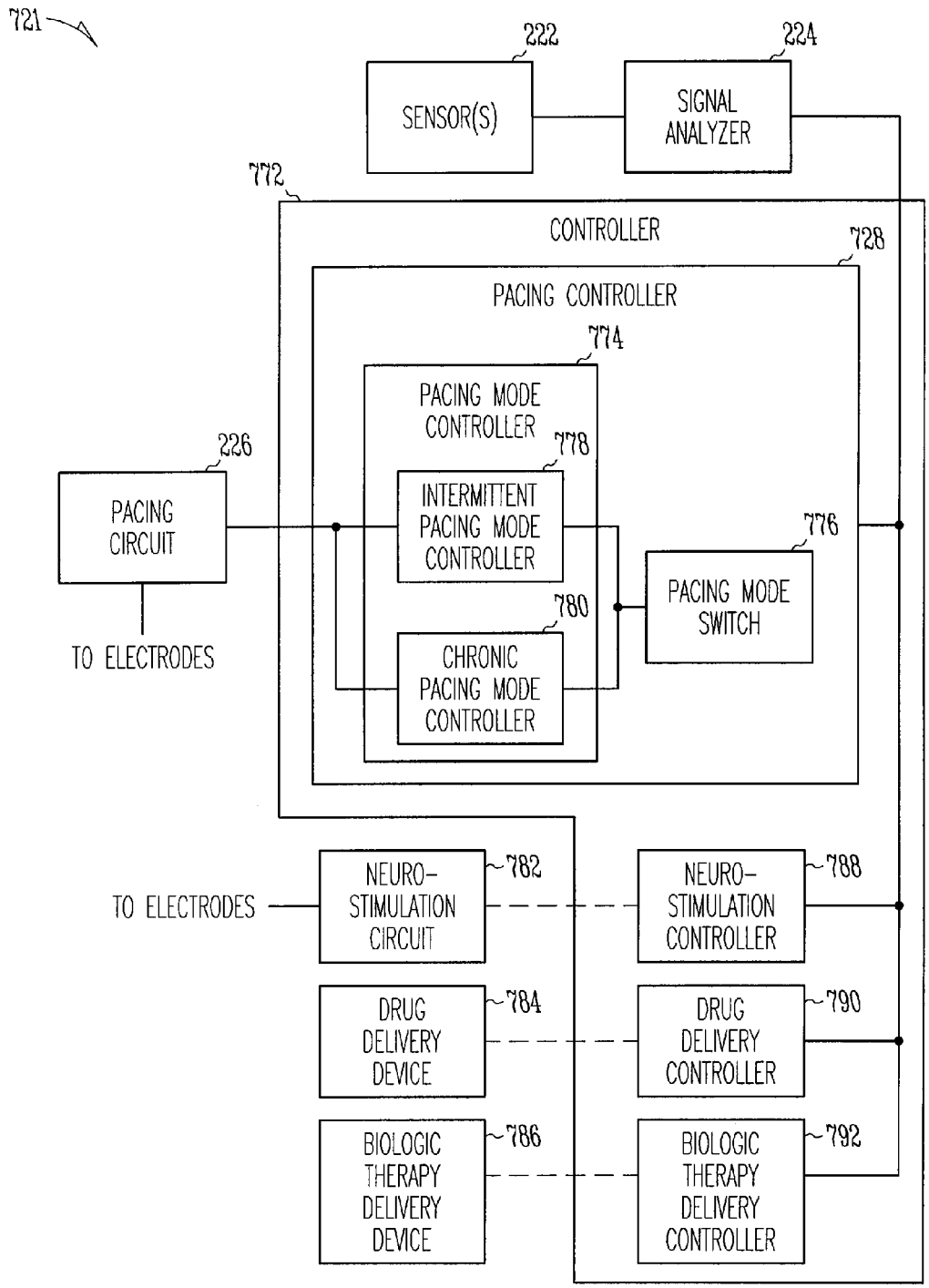
FIG. 7 is a block diagram illustrating an embodiment of portions of the CRM system including the intermittent pacing system and other therapeutic systems.

FIG. 7 is a block diagram illustrating an embodiment of portions of CRM system 100 including a system 721. System 721 includes intermittent pacing system 120 and other therapeutic systems. In the illustrated embodiment, system 721 includes sensor(s) 222, signal analyzer 224, pacing circuit 226, a controller 772, a neurostimulation circuit 782, a drug delivery device 784, and a biologic therapy delivery device 786. Neurostimulation circuit 782 delivers neurostimulation to body 102. Drug delivery device 784 delivers a drug therapy to body 102. Biologic therapy delivery device 786 delivers a biologic therapy such as a cell therapy or a gene therapy to body 102. In one embodiment, implantable medical device 110 includes one or more of neurostimulation circuit 782, drug delivery device 784, and biologic therapy delivery device 786. In another embodiment, CRM system 100 includes additional one or more implantable and/or non-implantable medical devices communicatively coupled to implantable medical device 110 and including one or more of neurostimulation circuit 782, drug delivery device 784, and biologic therapy delivery device 786.

In the illustrated embodiment, controller 772 includes a pacing controller 728, a neurostimulation controller 788, a drug delivery controller 790, and a biologic therapy delivery controller 792. In other embodiments, the therapeutic delivery devices of system 721 includes pacing circuit 226 and any one or more of neurostimulation circuit 782, drug delivery device 784, and biologic therapy delivery device 786, and controller 772 includes pacing controller 728 and the corresponding one or more of neurostimulation controller 788, drug delivery controller 790, and biologic therapy delivery controller 792.

Pacing controller 728 controls the delivery of the pacing pulses according to the cardiac stress augmentation pacing sequence as well as other pacing algorithms. This allows the function of cardiac stress augmentation pacing to be included in an implantable medical device that delivers pacing therapies on a long-term basis, such as for treatment of bardycardia or heart failure. Pacing controller 728 includes a pacing mode controller 774 and a pacing mode switch 776. Pacing mode controller 774 controls the delivery of the pacing pulses from pacing circuit 226 according to a selected pacing mode and includes an intermittent pacing mode controller 778 and a chronic pacing mode controller 780. Intermittent pacing mode controller 778 controls the delivery of pacing pulses according to an intermittent pacing mode. Chronic pacing mode controller 780 controls the delivery of pacing pulses according to a chronic pacing mode. In one embodiment, the cardiac stress augmentation pacing sequence is an intermittent pacing therapy delivered for short periods of time, while implantable medical device 110 also delivers a chronic pacing therapy such as a bardycardia pacing therapy, CRT, or RCT. The intermittent pacing mode is the pacing mode of the cardiac stress augmentation pacing sequence. The chronic pacing mode is the mode according to which pacing pulses are delivered as needed between cardiac stress augmentation pacing sequences. Pacing mode switch 776 switches the pacing mode from the chronic pacing mode to the intermittent pacing mode when the cardiac stress augmentation pacing sequence is initiated and to switch the pacing mode from the intermittent pacing mode to the chronic pacing mode when the cardiac stress augmentation pacing sequence is completed.

Neurostimulation controller 788 controls the delivery of neurostimulation from neurostimulation circuit 782. Drug delivery controller 790 controls the delivery of drug therapy from drug delivery device 784. Biologic therapy delivery controller 792 controls the delivery of biologic therapy from biologic therapy delivery device 786. In one embodiment, controller 772 coordinates the delivery of one or more of a pacing therapy, a neurostimulation therapy, a drug therapy, and a biologic therapy to treat the cardiac disorder such as heart failure. The coordinated delivery of therapies enhances the effects of the individual therapies in treating symptoms and slowing the progression of the cardiac disorder.

Figure 8:
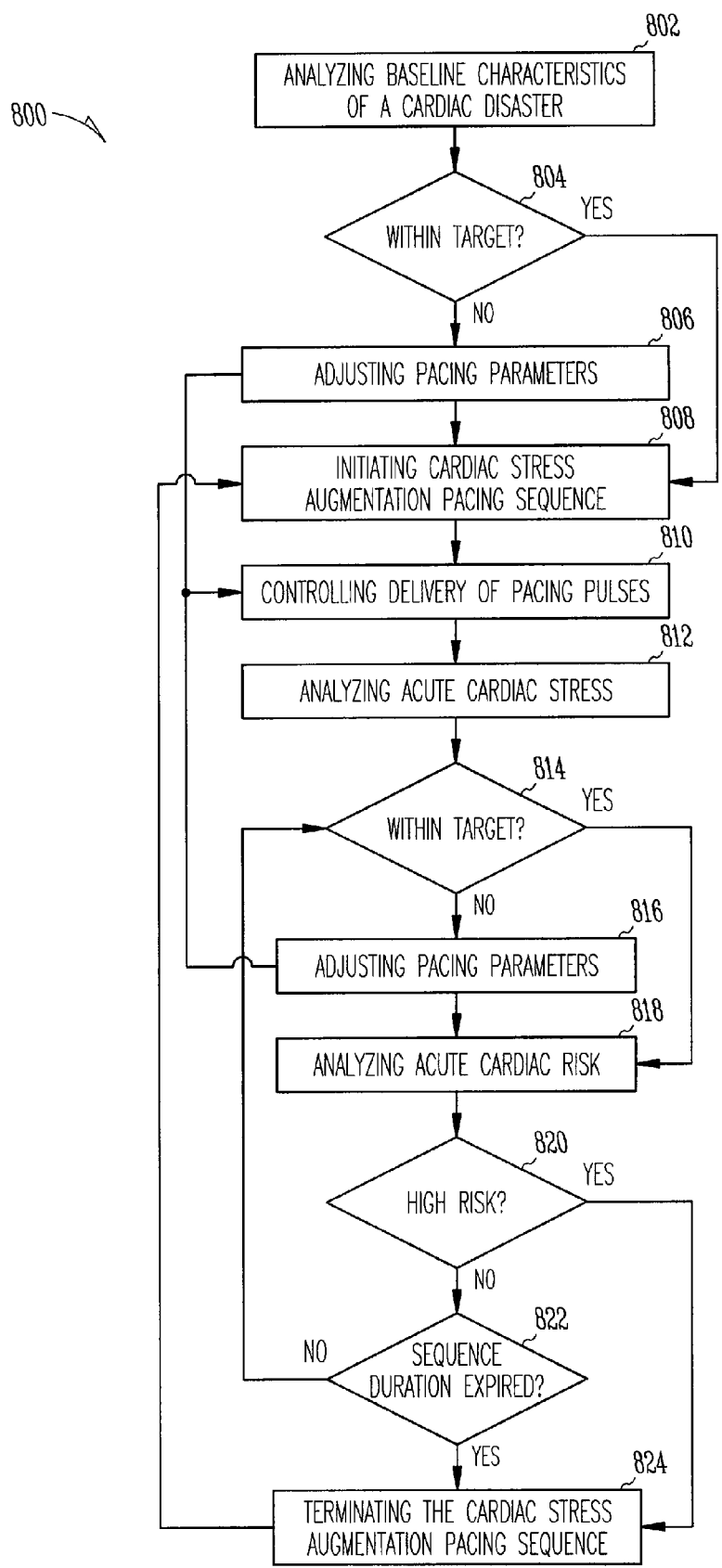
FIG. 8 is a flow chart illustrating a method for cardiac stress augmentation using intermittent pacing.
Figure 9:
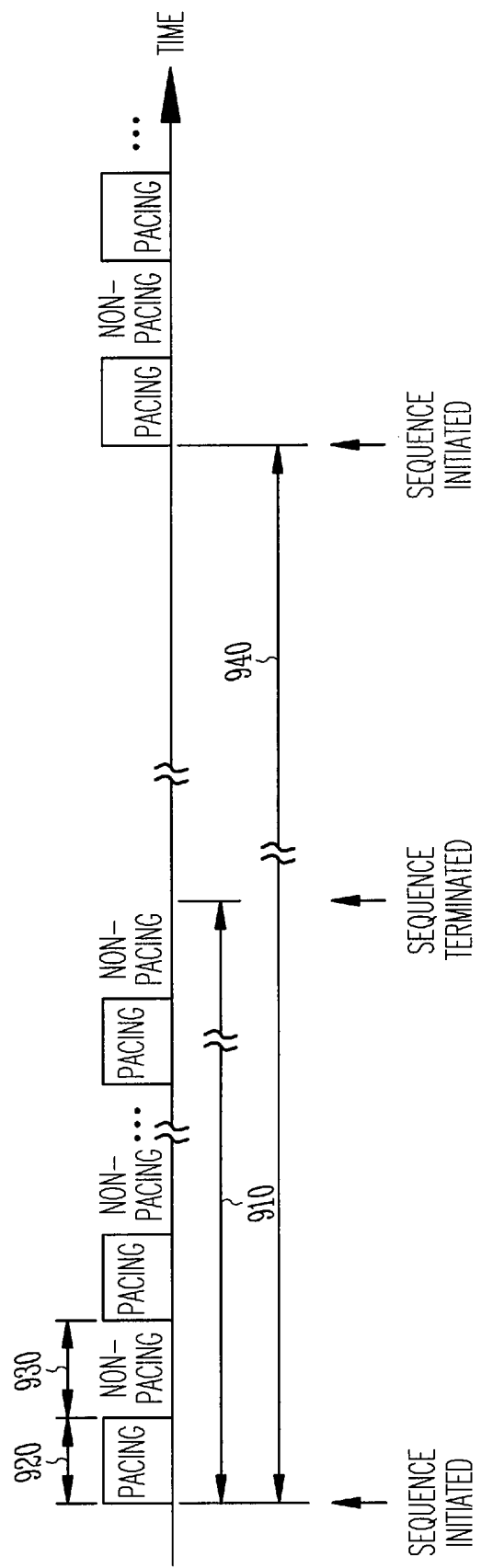
FIG. 9 is a timing diagram illustrating timing of an intermittent pacing therapy for cardiac stress augmentation.

FIG. 8 is a flow chart illustrating a method 800 for cardiac stress augmentation using intermittent pacing. The cardiac stress augmentation activates or enhances intrinsic mechanisms resisting or reversing progression of a cardiac disorder such as heart failure. The intermittent pacing is delivered as cardiac stress augmentation pacing sequences each delivered according to predetermined schedule and/or conditions. A timing example of the cardiac stress augmentation pacing sequences is illustrated in FIG. 9. The pacing parameters used to control the delivery of cardiac pacing pulses during the cardiac stress augmentation pacing sequences are adjusted using one or more sensed signals indicative of progression of the cardiac disorder, a level of acute cardiac stress, and a degree of cardiac risk associated with cardiac stress. In one embodiment, method 800 is performed by intermittent pacing systems discussed above with reference to FIGS. 1-7.

Baseline characteristics of the cardiac disorder are analyzed at 802. One or more baseline characteristic signals, each being a physiological signal, are sensed to indicate progression of the cardiac disorder. One or more baseline characteristic parameters indicative of progression of the cardiac disorder are produced using the one or more baseline characteristic signals. In one embodiment, a trend for selected one or more baseline characteristic parameters are produced, such as on a periodic basis. In one embodiment, the one or more baseline characteristic parameters are indicative of progression of heart failure. Examples of such baseline characteristic parameters include an HRV parameter produced using one or more cardiac signals, an activity level produced using an activity signal such as an accelerometer signal, a systolic blood pressure produced using a pressure signal, and cardiac chamber diameter, cardiac wall thickness, and cardiac chamber volume produced using cardiac dimension signals such as ultrasonic signals and impedance signals.

If the one or more baseline characteristic parameters indicate that the baseline characteristics of the cardiac disorder are not within a specified target at 804, the pacing parameters for the cardiac stress augmentation pacing sequences are adjusted at 806. Otherwise, pacing parameters for the cardiac stress augmentation pacing sequences remain unchanged. The target is specified with at least one threshold value for each of the one or more baseline characteristic parameters. The pacing parameters are adjusted at 806 as a function of the one or more baseline characteristic parameters. In one embodiment, the pacing parameters are adjusted to increase the level of cardiac stress augmentation if the one or more baseline characteristic parameters indicate a slowed progression of the cardiac disorder, thereby increasing the beneficial effects of the therapy. The pacing parameters are adjusted to decrease the level of cardiac stress augmentation if the one or more baseline characteristic parameters indicate an accelerated progression of the cardiac disorder, thereby protecting the patient from unintended and potentially harmful effects.

A cardiac stress augmentation pacing sequence is initiated at 808. In one embodiment, the cardiac stress augmentation pacing sequences are each initiated according to a predetermined schedule, such as on a periodic basis. In another embodiment, the cardiac stress augmentation pacing sequences are each initiated according to the predetermined schedule and the patient's activity level, such that each cardiac stress augmentation pacing sequence is initiated when the patient is in a resting state. The delivery of pacing pulses is controlled using the pacing parameters for the cardiac stress augmentation pacing sequences at 810.

Acute cardiac stress associated with the delivery of pacing pulses during the initiated cardiac stress augmentation pacing sequence is analyzed at 812. One or more stress signals, each being a physiological signal, are sensed to indicate a level of acute cardiac stress. One or more stress parameters indicative of the level of acute cardiac stress are produced using the one or more stress signals. Examples of such stress parameters include an asynchrony parameter indicative of a degree of cardiac asynchrony produced using one or more sensed impedance signals and a contractility parameter being a measure of cardiac contractility produced using a sensed blood pressure signal.

If the one or more stress parameters indicate that the level of acute cardiac pressure is not within a specified target at 814, the pacing parameters for the cardiac stress augmentation pacing sequences are adjusted at 816. Otherwise, pacing parameters for the cardiac stress augmentation pacing sequences remain unchanged. The pacing parameters are adjusted at 816 as a function of the one or more stress parameters such that the one or more stress parameters approach a target region. The target region is specified by at least one threshold value for each of the one or more stress parameters.

Cardiac risk associated with the delivery of the pacing pulses during the cardiac stress augmentation pacing sequence is analyzed at 818. One or more risk signals, each being a physiological signal, are sensed to indicate a degree of cardiac risk associated with cardiac stress. One or more risk parameters indicative of the degree of cardiac risk are produced using the one or more risk signals. Examples of such risk parameters include a systolic and diastolic blood pressures produced using a blood pressure signal.

If the one or more risk parameters indicate high risk at 820, the cardiac stress augmentation pacing sequence is terminated at 824. The high risk is indicated when the one or more risk parameters fall within a predetermined unsafe region.

The unsafe region is specified with at least one threshold value for each of the one or more risk parameters. If the one or more risk parameters does not indicate high risk at 820, but the sequence duration has expired at 822, the cardiac stress augmentation pacing sequence is terminated at 824.

FIG. 9 is a timing diagram illustrating the timing for an intermittent pacing therapy for cardiac stress augmentation. The intermittent pacing therapy includes delivery of pacing pulses according to the cardiac stress augmentation pacing sequences as discussed above. As illustrated in FIG. 9, the cardiac stress augmentation pacing sequences each have a sequence duration 910 and include alternating pacing and non-pacing periods. The pacing periods each have a pacing duration 920 during which pacing pulses are delivered. The non-pacing periods each have a non-pacing duration 930 during which no pacing pulse is delivered. In one embodiment, the cardiac stress augmentation pacing sequences are scheduled to initiate on a periodic basis with a cardiac stress augmentation period 940. In a further embodiment, the cardiac stress augmentation pacing sequences are each delivered while the patient is in a state of resting or low metabolic demand as indicated by one or more sensed physiological signals. Examples of such physiological signals include an activity signal indicative of the patient's gross activity level, a posture signal indicative of the patient's posture, a respiratory signal indicative of the patient's respiratory pattern, and a cardiac signal indicative of the patient's heart rate. If cardiac stress augmentation period 940 expires while the patient is at a state of exercise or high metabolic demand, the initiation of the cardiac stress augmentation pacing sequence is delayed until the patient enters the state of resting or low metabolic demand, such as when the gross activity level falls below a predetermined threshold.

In one embodiment, sequence duration 910 is programmable between 5 minutes and 90 minutes. Alternatively, sequence duration 910 is defined by programming the number of pacing periods during the cardiac stress augmentation pacing sequence. Pacing duration 920 is programmable between 1 minute and 60 minutes. Non-pacing duration 930 is programmable between 1 minute and 60 minutes. Cardiac stress augmentation pacing period 940 is programmable between 3 hours and 96 hours.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A cardiac rhythm management (CRM) system, comprising:
   one or more sensors to sense one or more physiological signals;
   a pacing circuit to deliver cardiac pacing pulses;
   a signal analyzer coupled to the one or more sensors, the signal analyzer adapted to produce one or more physiological parameters indicative of progression of heart failure and a level of acute cardiac stress created by delivery of the cardiac pacing pulses during a cardiac stress augmentation pacing sequence using the one or more physiological signals, the one or more physiological parameters including an asynchrony parameter indicative of a degree of cardiac asynchrony;
   a pacing controller coupled to the signal analyzer and the pacing circuit, the pacing controller adapted to control the delivery of the cardiac pacing pulses and increase the degree of cardiac asynchrony by adjusting one or more pacing parameters using feedback control using the one or more physiological parameters, the pacing controller including:
      a stress augmentation pacing initiator adapted to initiate the cardiac stress augmentation pacing sequence having the one or more pacing parameters and a sequence duration and including alternating pacing and non-pacing periods, the pacing periods each having a pacing duration during which a plurality of the cardiac pacing pulses is delivered, the non-pacing periods each having a non-pacing duration during which none of the cardiac pacing pulses is delivered;
      a stress augmentation pacing timer adapted to time the cardiac stress augmentation pacing sequence; and
      a pacing parameter adjuster adapted to adjust the one or more pacing parameters using the one or more physiological parameters.

2. The system of claim 1, wherein the one or more sensors comprise one or more baseline characteristic sensors adapted to sense one or more baseline characteristic signals indicative of the progression of heart failure, the signal analyzer comprises a baseline characteristic analyzer adapted to produce one or more baseline characteristic parameters indicative of the progression of heart failure using the one or more baseline characteristic signals, and the pacing parameter adjuster is adapted to adjust the pacing parameters using the one or more baseline characteristic parameters.

3. The system of claim 2, wherein the baseline characteristic analyzer is adapted to produce a trend for at least one of the one or more baseline characteristic parameters.

4. The system of claim 2, wherein the one or more baseline characteristic sensors comprise an activity sensor to sense an activity signal, and the baseline characteristic analyzer comprises an activity analyzer adapted to produce an activity level parameter using the activity signal.

5. The system of claim 2, wherein the one or more baseline characteristic sensors comprise a pressure sensor to sense a blood pressure signal, and the baseline characteristic analyzer comprises a pressure analyzer adapted to produce a systolic blood pressure parameter using the blood pressure signal.

6. The system of claim 2, wherein the one or more baseline characteristic sensors comprise one or more cardiac dimension sensors to sense one or more signals indicative of cardiac dimensions, and the baseline characteristic analyzer comprises a cardiac dimension analyzer adapted to produce one or more cardiac size parameters using the one or more signals indicative of cardiac dimensions, the one or more cardiac size parameters indicative of one or more of a cardiac chamber diameter, a cardiac wall thickness, and a cardiac volume.

7. The system of claim 2, wherein the one or more baseline characteristic sensors comprise a cardiac sensing circuit to sense one or more cardiac signals, and the baseline characteristic analyzer comprises a heart rate variability (HRV) analyzer adapted to produce an HRV parameter using the one or more cardiac signals.

8. The system of claim 1, wherein the one or more sensors comprise one or more stress sensors adapted to sense one or more stress signals indicative of the level of acute cardiac stress, the signal analyzer comprises a stress analyzer adapted to produce one or more stress parameters indicative of the level of acute cardiac stress using the one or more stress signals, and the pacing parameter adjuster is adapted to adjust the pacing parameters using the one or more stress parameters such that the one or more stress parameters approach a target value region specified with one or more values of the one or more stress parameters.

9. The system of claim 8, wherein the one or more stress sensors comprise an impedance sensor to sense an impedance signal, and the stress analyzer comprises an asynchrony analyzer adapted to produce the asynchrony parameter indicative of the degree of cardiac asynchrony using the impedance signal.

10. The system of claim 8, wherein the one or more stress sensors comprise a pressure sensor to sense a blood pressure signal, and the stress analyzer comprises a contractility analyzer adapted to produce a contractility parameter being a measure of cardiac contractility using the blood pressure signal.

11. The system of claim 1, wherein the one or more sensors comprise one or more risk sensors adapted to sense one or more risk signals indicative of a degree of cardiac risk associated with cardiac stress, the signal analyzer comprises a risk analyzer adapted to produce one or more risk parameters indicative of cardiac risk using the one or more risk signals.

12. The system of claim 11, wherein the one or more risk sensors comprise a pressure sensor to sense a blood pressure signal, and the risk analyzer comprises one or more of a cardiac output analyzer adapted to produce a systolic blood pressure and a diastolic function analyzer adapted to produce a diastolic blood pressure using the blood pressure signal.

13. The system of claim 11, wherein the pacing controller comprises a safety switch adapted to stop the cardiac stress augmentation pacing sequence if the one or more risk parameters fall within a predetermined risk zone defined by one or more threshold values.

14. The system of claim 1, wherein the stress augmentation pacing initiator is adapted to initiate the cardiac stress augmentation pacing sequence according to a cardiac stress augmentation pacing schedule and at least one of the one or more physiological signals.

15. The system of claim 1, wherein the pacing controller comprises a pacing mode switch adapted to switch a pacing mode from a chronic pacing mode to an intermittent pacing mode when the cardiac stress augmentation pacing sequence is initiated and to switch the pacing mode from the intermittent pacing mode to the chronic pacing mode when the cardiac stress augmentation pacing sequence is completed.

16. The system of claim 1, further comprising one or more non-pacing therapy devices adapted to deliver one or more non-pacing therapies, and a non-pacing therapy controller adapted to control the delivery of the one or more non-pacing therapies using the one or more physiological parameters.

17. The system of claim 16, comprising:
an implantable medical device including at least the pacing circuit, the pacing controller, and the non-pacing controller; and
one or more additional medical devices each communicatively coupled to the implantable medical device, the one or more additional medical devices each including at least one of the one or more non-pacing therapy devices.

18. The system of claim 1, wherein the pacing parameter adjuster is adapted to adjust one or more of an atrioventricular delay and an interventricular delay of the one or more pacing parameters.

19. A method for operating a cardiac rhythm management (CRM) system, the method comprising:
sensing one or more physiological signals;
producing one or more physiological parameters indicative of progression of heart failure and a level of acute cardiac stress created by delivery of cardiac pacing pulses during a cardiac stress augmentation pacing sequence using the one or more physiological signals, the one or more physiological parameters including an asynchrony parameter indicative of a degree of cardiac asynchrony;
delivering the cardiac pacing pulses according to the cardiac stress augmentation pacing sequence having one or more pacing parameters and a sequence duration and including alternating pacing and non-pacing periods, the pacing periods each having a pacing duration during which a plurality of the cardiac pacing pulses is delivered, the non-pacing periods each having a non-pacing duration during which none of the cardiac pacing pulses is delivered; and
increasing the degree of cardiac asynchrony by adjusting the one or more pacing parameters using feedback control using the one or more physiological parameters.

20. The method of claim 19, wherein adjusting the one or more pacing parameters comprises adjusting an atrioventricular delay.

21. The method of claim 19, wherein adjusting the one or more pacing parameters comprises adjusting an interventricular delay.

22. The method of claim 19, wherein sensing the one or more physiological signals comprises sensing one or more baseline characteristic signals indicative of the progression of heart failure, producing the one or more physiological parameters comprises producing one or more baseline characteristic parameters indicative of progression of heart failure using the one or more baseline characteristic signals, and adjusting the one or more pacing parameters comprises adjusting the one or more pacing parameters using the one or more baseline characteristic parameters.

23. The method of claim 22, wherein producing the one or more physiological parameters comprises producing a trend for at least one of the one or more baseline characteristic parameters, and adjusting the one or more pacing parameters comprises adjusting the one or more pacing parameters using the trend.

24. The method of claim 22, wherein sensing the one or more baseline characteristic signals comprises sensing one or more of a cardiac signal, an activity signal, a blood pressure signal, and a cardiac dimension signal, and producing the one or more physiological parameters comprises one or more of producing a heart rate variability (HRV) parameter using the cardiac signal, producing an activity level parameter using the activity signal, producing a systolic blood pressure parameter using the blood pressure signal, and producing one or more cardiac size parameters using the cardiac dimension signal.

25. The method of claim 19, wherein sensing the one or more physiological signals comprises sensing one or more stress signals indicative of a level of acute cardiac stress, producing the one or more physiological parameters comprises producing one or more stress parameters indicative of the level of acute cardiac stress using one or more stress signals, and adjusting the one or more pacing parameters comprises adjusting the one or more pacing parameters using the one or more stress parameters such that the one or more stress parameters approach a target value region specified with one or more values of the one or more stress parameters.

26. The method of claim 25, wherein sensing the one or more stress signals comprises sensing one or more of an impedance signal, a blood pressure signal and a strain signal, and producing the one or more stress parameters comprises one or more of producing the asynchrony parameter indicative of the degree of cardiac asynchrony using the impedance signal and producing a contractility parameter being a measure of cardiac contractility using at least one of the blood pressure signal and the strain signal.

27. The method of claim 19, wherein sensing the one or more physiological signals comprises sensing one or more risk signals indicative of a degree of cardiac risk associated with cardiac stress, and producing the one or more physiological parameters comprises producing one or more risk parameters indicative of cardiac risk using the one or more risk signals.

28. The method of claim 27, wherein sensing the one or more risk signals comprises sensing one or more of a blood pressure signal and a neurohormonal signal, and producing the one or more risk parameters comprises one or more of producing a systolic blood pressure using the blood pressure signal, producing a diastolic blood pressure using the blood pressure signal, and producing a neurohormonal level using the neurohormonal signal.

29. The method of claim 27, further comprising stopping the delivery of the cardiac pacing pulses according to the cardiac stress augmentation pacing sequence if the one or more risk parameters fall within a predetermined risk zone defined by one or more threshold values.

30. The method of claim 19, further comprising initiating the cardiac stress augmentation pacing sequence on an approximately periodic basis using a stress augmentation pacing period programmable between 3 hours and 96 hours, and programming the sequence duration to a duration between 5 minutes and 90 minutes.

31. The method of claim 19, further comprising initiating the cardiac stress augmentation pacing sequence according to a cardiac stress augmentation pacing schedule and one or more of an activity signal, a posture signal, a respiratory signal, and a cardiac signal.

* * * * *